US011007098B2

(12) United States Patent
Ribble et al.

(10) Patent No.: US 11,007,098 B2
(45) Date of Patent: May 18, 2021

(54) LAYERED GRADUATED LATERAL ROTATION APPARATUS

(71) Applicant: Hill-Rom Services, Inc., Batesville, IN (US)

(72) Inventors: David L. Ribble, Batesville, IN (US); Kirsten M. Emmons, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 393 days.

(21) Appl. No.: 16/022,846

(22) Filed: Jun. 29, 2018

(65) Prior Publication Data

US 2019/0015278 A1 Jan. 17, 2019

Related U.S. Application Data

(60) Provisional application No. 62/531,981, filed on Jul. 13, 2017.

(51) Int. Cl.
| | |
|---|---|
| *A61G 7/07* | (2006.01) |
| *A61F 5/56* | (2006.01) |
| *A61G 7/075* | (2006.01) |
| *A61G 7/015* | (2006.01) |
| *A47C 20/04* | (2006.01) |

(52) U.S. Cl.
CPC .................. *A61G 7/07* (2013.01); *A61F 5/56* (2013.01); *A61G 7/015* (2013.01); *A61G 7/0755* (2013.01); *A47C 20/04* (2013.01)

(58) Field of Classification Search
None
See application file for complete search history.

(56) References Cited

U.S. PATENT DOCUMENTS

| | | | |
|---|---|---|---|
| 3,775,785 A | 12/1973 | Mittendorf | |
| 4,754,510 A | 7/1988 | King | |
| 4,807,313 A | 2/1989 | Ryder et al. | |
| 5,092,007 A | 3/1992 | Hasty | |

(Continued)

FOREIGN PATENT DOCUMENTS

| | | | |
|---|---|---|---|
| DE | 4137631 A1 | 5/1992 | |
| EP | 262771 A1 | 4/1988 | |

(Continued)

OTHER PUBLICATIONS

Adesanya, Adebola O., et al., *Perioperative Management of Obstructive Sleep Apnea*, Chest/138/6, Dec. 2010 (10 pages).

(Continued)

*Primary Examiner* — David R Hare
*Assistant Examiner* — Adam C Ortiz
(74) *Attorney, Agent, or Firm* — Barnes & Thornburg LLP

(57) ABSTRACT

A lateral rotation apparatus is provided having a wedge positioned below a person support surface having head, torso and leg segments each having an independently rotatable person support plane. The wedge includes a plurality of layers stacked on one another. Each of the plurality of layers has a different area. The wedge is operable to rotate the head segment of the person support surface to a head tilt angle relative to a horizontal support plane. The wedge is also operable to rotate the torso segment of the person support surface to a torso tilt angle relative to the horizontal support plane.

20 Claims, 13 Drawing Sheets

(56) References Cited

U.S. PATENT DOCUMENTS

| | | |
|---|---|---|
| 5,097,551 A | 3/1992 | Smith |
| 5,611,096 A | 3/1997 | Bartlett et al. |
| 5,640,729 A | 6/1997 | Marino |
| 5,745,937 A | 5/1998 | Weismiller et al. |
| 5,754,998 A | 5/1998 | Selton |
| 5,910,080 A | 6/1999 | Selton |
| 5,966,762 A | 10/1999 | Wu |
| 6,047,419 A | 4/2000 | Ferguson |
| 6,081,950 A | 7/2000 | Selton |
| 6,154,900 A | 12/2000 | Shaw |
| 6,163,903 A | 12/2000 | Weismiller et al. |
| D446,676 S | 8/2001 | Mayes |
| 6,370,716 B1 | 4/2002 | Wilkinson |
| 6,485,441 B2 | 11/2002 | Woodward |
| 6,536,056 B1 | 3/2003 | Vrzalik et al. |
| 6,578,219 B1 | 6/2003 | Gabel et al. |
| 6,671,907 B1 | 1/2004 | Zuberi |
| 6,681,424 B1 | 1/2004 | Bourgraf et al. |
| 6,751,817 B1 | 6/2004 | Leach |
| 6,904,631 B2 | 6/2005 | Vrzalik et al. |
| 7,007,327 B2 | 3/2006 | Ogawa et al. |
| 7,017,213 B2 | 3/2006 | Chisari |
| 7,089,615 B1 | 8/2006 | Parimuha |
| D527,937 S | 9/2006 | Aiken et al. |
| 7,346,945 B2 | 3/2008 | Phillips et al. |
| 7,346,951 B1 * | 3/2008 | Heaton ................ A61G 7/008 5/615 |
| 7,418,751 B1 | 9/2008 | Bartlett et al. |
| 7,464,422 B2 | 12/2008 | Townsend |
| 7,513,003 B2 | 4/2009 | Mossbeck |
| 7,654,974 B2 | 2/2010 | Bass |
| 7,690,059 B2 | 4/2010 | Lemire et al. |
| 7,805,784 B2 | 10/2010 | Lemire et al. |
| 7,861,334 B2 | 1/2011 | Lemire et al. |
| 7,886,379 B2 | 2/2011 | Benzo et al. |
| 7,962,981 B2 | 6/2011 | Lemire et al. |
| 7,975,335 B2 | 7/2011 | O'Keefe et al. |
| 8,006,332 B2 | 8/2011 | Lemire et al. |
| 8,220,091 B2 | 7/2012 | Schultz |
| 8,261,380 B2 | 9/2012 | Ferraresi et al. |
| 8,356,602 B2 | 1/2013 | Crocetti |
| 8,393,026 B2 | 3/2013 | Dionne et al. |
| 8,413,271 B2 | 4/2013 | Blanchard et al. |
| 8,544,126 B2 | 10/2013 | Elliott et al. |
| 8,661,586 B2 | 3/2014 | Melcher et al. |
| 8,689,376 B2 | 4/2014 | Becker et al. |
| 8,695,134 B2 | 4/2014 | Schultz |
| 8,701,229 B2 | 4/2014 | Lemire et al. |
| 8,720,447 B2 | 5/2014 | North |
| 8,756,736 B1 | 6/2014 | Minson |
| 8,789,222 B2 | 7/2014 | Blanchard et al. |
| 8,832,887 B2 | 9/2014 | Mossbeck |
| 8,844,076 B2 | 9/2014 | Becker et al. |
| 8,870,764 B2 | 10/2014 | Rubin |
| 9,038,217 B2 | 5/2015 | Elliot et al. |
| 9,126,571 B2 | 9/2015 | Lemire et al. |
| 2006/0179580 A1 | 8/2006 | Robertson et al. |
| 2007/0163051 A1 | 7/2007 | Straub |
| 2008/0109965 A1 | 5/2008 | Mossbeck |
| 2008/0148487 A1 | 6/2008 | Lord et al. |
| 2009/0250070 A1 | 10/2009 | Pfeifer |
| 2011/0231996 A1 | 9/2011 | Lemire et al. |
| 2012/0138067 A1 | 6/2012 | Rawls-Meehan |
| 2012/0222214 A1 | 9/2012 | Lachenbruch et al. |
| 2013/0198965 A1 | 8/2013 | Melcher et al. |
| 2013/0245395 A1 | 9/2013 | Bidarian Moniri |
| 2014/0059768 A1 | 3/2014 | Lemire et al. |
| 2014/0088373 A1 | 3/2014 | Phillips et al. |
| 2014/0173829 A1 | 6/2014 | Melcher et al. |
| 2014/0180036 A1 | 6/2014 | Bukkapatnam et al. |
| 2014/0245539 A1 | 9/2014 | Ooba |
| 2014/0259417 A1 | 9/2014 | Nunn et al. |
| 2014/0259418 A1 | 9/2014 | Nunn et al. |
| 2014/0259419 A1 | 9/2014 | Stusynski et al. |
| 2014/0259433 A1 | 9/2014 | Nunn et al. |
| 2014/0259434 A1 | 9/2014 | Nunn et al. |
| 2014/0266733 A1 | 9/2014 | Hayes et al. |
| 2014/0277611 A1 | 9/2014 | Nunn et al. |
| 2014/0283302 A1 | 9/2014 | Horstmann |
| 2014/0366274 A1 | 12/2014 | Melcher et al. |
| 2015/0000035 A1 | 1/2015 | Becker et al. |
| 2015/0335507 A1 * | 11/2015 | Emmons ................ G16H 50/30 5/615 |
| 2017/0277822 A1 | 9/2017 | Clark et al. |

FOREIGN PATENT DOCUMENTS

| | | |
|---|---|---|
| EP | 2140847 A2 | 1/2010 |
| EP | 2175822 A1 | 4/2010 |
| EP | 2494946 A2 | 9/2012 |
| JP | 2011143237 A | 7/2011 |
| KR | 20110083167 A | 7/2011 |
| WO | 2010048310 A1 | 4/2010 |
| WO | 2013031504 A1 | 3/2013 |
| WO | 2013116676 A1 | 8/2013 |
| WO | 2013166003 A1 | 11/2013 |
| WO | 2013177338 A2 | 11/2013 |
| WO | 2014069713 A1 | 5/2014 |
| WO | 2014149392 A1 | 9/2014 |
| WO | 2014151707 A1 | 9/2014 |
| WO | 2014152891 A1 | 9/2014 |

OTHER PUBLICATIONS

Ankichetty, Saravanan and Frances Chung, *Considerations for Patients with Obstructive Sleep Apnea Undergoing Ambulatory Surgery*, Current Opinion in Anesthesiology 2011, 24:605-611 (7 pages).

Arnold, Donald H., et al., *Estimation of Airway Obstruction Using Oximeter Plethysmograph Waveform Data*, Respiratory Research 2005, 6:65 (8 pages).

American Society of Anesthesiologists, Inc., *Practice Guidelines for the Perioperative Management of Patients with Obstructive Sleep Apnea*, Anesthesiology 2006, V. 104, 1081-93, No. 5, May 2006, (13 pages).

Benumof, Jonathan L., *Obstructive Sleep Apnea in the Adult Obese Patient: Implications for Airway Management*, Journal of Clinical Anesthesia 13:144-156, 2001 (13 pages).

Berend, Keith R., et al., *Prevalence and Management of Obstructive Sleep Apnea in Patients Undergoing Total Joint Arthroplasty*, The Journal of Arthroplasty vol. 25 No. 6 Suppl. 1 2010 (4 pages).

Berger, G., et al., *Progression of Snoring and Obstructive Sleep Apnoea: The Role of Increasing Weight and Time*, European Respiratory Journal, vol. 33, No. 2, 2009 (8 pages).

Bianchi, Matt T., *Screening for Obstructive Sleep Apnea: Bayes Weighs In*, The Open Sleep Hournal, 2009, 2, 56-59 (4 pages).

Bignold, James J., et al., *Accurate Position Monitoring and Improved Supine-Dependent Obstructive Sleep Apnea with a New Position Recording and Supine Avoidance Device*, Journal of Clinical Sleep Medicine, vol. 7, No. 4, 2001 (8 pages).

Bloom, Harrison G., et al., *Evidence-Based Recommendations for the Assessment and Management of Sleep Disorders in Older Persons*, J Am Geriatr Soc 57:761-789, 2009 (30 pages).

Bolden, Norman, et al., *Avoiding Adverse Outcomes in Patients with Obstructive Sleep Apnea (OSA): Development and Implementation of a Perioperative OSA Protocol*, Journal of Clinical Anesthesia (2009) 21, 286-293 (8 pages).

Bourne, Richard S., et al., *Clinical Review: Sleep Measurement in Critical Care Patients: Research and Clinical Implications*, Critical Care 2007, 11:226 (17 pages).

Brown, Carlos VR and George C. Velmahos, *The Consequences of Obesity on Trauma, Emergency Surgery, and Surgical Critical Care*, World Journal of Emergency Surgery 2006, 1:27 (5 pages).

Bush, Haydn, *Screening for Sleep Apnea*, American Hospital Association Health Forum, Hospital & Health Networks, hhn@omeda.com, 2013 (2 pages).

Camilo, Millene R., et al., *Supine Sleep and Positional Sleep Apnea After Acute Ischemic Stroke and Intracerebral Hemorrhage*, Clinics 2012; 67(12); 1357-1360 (4 pages).

(56) References Cited

OTHER PUBLICATIONS

Carr, Gordon E., et al., *Acute Cardiopulmonary Failure From Sleep-Disordered Breathing*, Chest 2012; 141(3); 798-808 (11 pages).
Casey, Kenneth R. and Michael J. Lefor, *Management of the Hospitalized Patient with Sleep Disordered Breathing*, Current Opinion in Pulmonary Medicine 2002, 8:511-515 (5 pages).
Chia, P., et al., *The Association of Pre-Operative Stop-Bang Scores with Postoperative Critical Care Admission*, Anaesthesia 2013, 68, 950-952 (3 pages).
Choi, Jae-Kap, et al., *Effect of Jaw and Head Position on Airway Resistance in Obstructive Sleep Apnea*, Sleep and Breathing, vol. 4, No. 4, 163-168, 2000 (8 pages).
Choi, Ji Ho, et al., *Efficacy Study of a Vest-Type Device for Positional Therapy in Position Dependent Snorers*, Sleep and Biological Rhythms 2009; 7; 181-187 (7 pages).
Chung, Sharon A., et al., *A Systemic Review of Obstructive Sleep Apnea and Its Implications for Anesthesiologists*, Ambulatory Anesthesiology, vol. 107, No. 5, Nov. 2008, 1543-1563 (21 pages).
Chung, F., et al., *High Stop-Band Score Indicates a High Probability of Obstructive Sleep Apnoea*, British Journal of Anaesthesia 108 (5): 768-75 (2012), (8 pages).
Chung, Frances and Babak Mokhlesi, *Postoperative Complications Associates with Obstructive Sleep Apnea: Time to Wake Up!*, Anesthesia & Analgesia, Feb. 2014, vol. 118, No. 2, 251-253 (3 pages).
Chung, Frances et al., *Preoperative Identification of Sleep Apnea Risk in Elective Surgical Patient6s, Using the Berlin Questionnaire*, Journal of Clinical Anesthesia (2007) 19, 130-134 (5 pages).
Chung, Frances and Hisham Elsaid, *Screening for Obstructive Sleep Apnea Before Surgery: Why is it Important?*, Current Opinion in Anaesthesiology 2009, 22:405-411 (7 pages).
Chung, Frances, et al., *Validation of the Berlin Questionnaire and American Society of Anesthesiologists Checklist as Screening Tools for Obstructive Sleep Apnea in Surgical Patients*, Anesthesiology, vol. 108, No. 5, May 2008, 822-830 (9 pages).
Curry, J. Paul and Lawrence A. Lynn, *Threshold Monitoring, Alarm Fatigue, and the Patterns of Unexpected Hospital Death*, The Official Journal of the Anesthesia Patient Safety Foundation, Fall 2011 (8 pages).
D'Apuzzo, Michele R. and James A. Browne, *Obstructive Sleep Apnea as a Risk Factor for Postoperative Complications After Revision Joint Arthroplasty*, The Journal of Arthroplasty, vol. 27, No. 8, Suppl. 1 (2012), 95-98 (4 pages).
Der Herder, Cindy, et al., *Risks of General Anaesthesia in People with Obstructive Sleep Apnoea*, British Medical Journal, vol. 329, Oct. 23, 2004, 955-959 (5 pages).
Dolezal, Donna, et al., *Implementing Preoperative Screening of Undiagnosed Obstructive Sleep Apnea*, Journal of PeriAnesthesia Nursing, vol. 26, No. 5 Oct. 2011, 338-342 (5 pages).
Ead, Heather, *Meeting the Challenge of Obstructive Sleep Apnea: Developing a Protocol that Guides Perianesthesia Patient Care*, Journal of PeriAnesthesia Nursing, vol. 24, No. 2 Apr. 2009, 103-113 (11 pages).
Farney, Robert J., et al., *The Stop-Bang Equivalent Model and Prediction of Severity of Obstructive Sleep Apnea: Relation to Polysomnographic Measurements of the Apnea/Hypopnea Index*, Journal of Clinical Sleep Medicine, vol. 7, No. 5, 2011, 459-467 (9 pages).
Finkel, Kevin J., et al., *Prevalence of Undiagnosed Obstructive Sleep Apnea Among Adult Surgical Patients in an Academic Medical Center*, Sleep Medicine 10 (2009) 753-758 (6 pages).
Finucane, Thomas E., *Evidence-Based Recommendations for the Assessment and Management of Sleep Disorders in Older Persons*, JAGS, Nov. 2009, vol. 57, No. 11, 2173-2174 (3 pages).
Fletcher, Eugene C., *"Near Miss" Death in Obstructive Sleep Apnea: A Critical Care Syndrome*, Critical Care Medicine, vol. 19, No. 9, Sep. 1991, 1158-1164 (7 pages).
Galhotra, Sanjay, *Mature Rapid Response System and Potentially Avoidable Cardiopulmonary Arrests in Hospital*, Qual. Saf. Health Care 2007, 16:260-265 (6 pages).

Gammon, Brian T. and Karen F. Ricker, *An Evidence-Based Checklist for the Postoperative Management of Obstructive Sleep Apnea*, Journal of PeriAnesthesia Nursing, vol. 27, No. 5 Oct. 2012, 316-322 (7 pages).
Gay, Peter C., *Sleep and Sleep-Disordered Breathing in the Hospitalized Patient*, Respiratory Care, Sep. 2010, vol. 55, No. 9, 1240-1254 (15 pages).
Gay, Peter C., *The Value of Assessing Risk of Obstructive Sleep Apnea in Surgical Patients: It Only Takes One*, Journal of Clinical Sleep Medicine, vol. 6, No. 5, 2010, 473-474 (2 pages).
Global Industry Analysts, Inc., *GIA Market Report: Sleep Apnea Diagnostic and Therapeutic Devices, A Global Strategic Business Report*, MCP-3307, Oct. 2010, www.StrategyR.com, (321 pages).
Gibson, G. J., *Obstructive Sleep Apnoea Syndrome: Underestimated and Undertreated*, British Medical Bulletin 2004; 72: 49-64 (16 pages).
Gupta, Rakesh M., et al., *Postoperative Complications in Patients With Obstructive Sleep Apnea Syndrome Undergoing Hip or Knee Replacement: A Case-Control Study*, May Clin Proc. 2001; 76:897-905 (9 pages).
Guralnick, Amy S., et al., *CPAP Adherence in Patients with Newly Diagnosed Obstructive Sleep Apnea Prior to Elective Surgery*, Journal of Clinical Sleep Medicine, vol. 8, No. 5, 2012, 501-506 (6 pages).
Heinzer, Raphael C., et al., *Positional Therapy for Obstructive Sleep Apnea: An Objective Measurement of Patients' Usage and Efficacy at Home*, Sleep Medicine 13 (2012) 425-428 (4 pages).
Hogue, Enamul, et al., *Monitoring Body Positions and Movements During Sleep Using WISPs*, Wireless Health '10, Oct. 5-7, 2010 (10 pages).
Isono, Shiroh, et al., *Lateral Position Decreases Collapsibility of the Passive Pharynx in Patients with Obstructive Sleep Apnea*, Anesthesiology, vol. 97, No. 4, Oct. 2002, 780-785 (6 pages).
Itasaka, Yoshiaki and Kazuo Ishikawa, *The Influence of Sleep Position and Obesity on Sleep Apnea*, Psychiatry and Clinical Neurosciences (2000), 54, 340-341 (3 pages).
Jensen, Candice, et al., *Postoperative CPAP and BiPAP Use Can be Safely Omitted after Laparoscopic Roux-en-Y Gastric Bypass*, Surgery for Obesity and Related Diseases 4 (2008) 512-514 (3 pages).
Joho, Shuji, et al., *Impact of Sleeping Position on Central Sleep Apnea/Cheyne-Stokes Respiration in Patients with Heart Failure*, Sleep Medicine 11 (2010) 143-148 (6 pages).
Jokie, Ruzica, et al., *Positional Treatment vs. Continuous Positive Airway Pressure in Patients with Positional Obstructive Sleep Apnea Syndrome*, Chest/115/3/Mar. 1999, 771-781 (11 pages).
Joosten, S.A., et al., *Obstructive Sleep Apnea Phenotypic Trait Changes from Supine to Lateral Position*, Am J Respir Crit Care Med 189; 2014; A3909 (1 page).
Joshi, Girish P., et al., *Society for Ambulatory Anesthesia Consensus Statement on Preoperative Selection of Adult Patients with Obstructive Sleep Apnea Scheduled for Ambulatory Surgery*, Anesthesia & Analgesia, Nov. 2012, vol. 115, No. 5, 1060-1068 (9 pages).
Keenan, Sean P., et al., *Clinical Practice Guidelines for the Use of Noninvasive Positive-Pressure Ventilation and Noninvasive Continuous Positive Airway Pressure in the Acute Care Setting*, Canadian Medical Association Journal, Feb. 22, 2011, 183(3) (21 pages).
Khayat, Rami, et al., *In-Hospital Resting for Sleep-Disordered Breathing in Hospitalized Patients with Decompensated Heart Failure: Report of Prevalence and Patient Characteristics*, Journal of Cardiac Failure, vol. 15, No. 9 (2009) (739-746).
Kim, Eun Joong, *The Prevalence and Characteristics of Positional Sleep Apnea in Korea*, Korean J Otorhinolaryngol-Head Neck Surg. 2009:52:407-12 (6 pages).
Kulkarni, Gaurav V., et al., *Obstructive Sleep Apnea in General Surgery Patients: Is it More Common than we Think?*, The American Journal of Surgery (2014) 207, 436-440 (5 pages).
Lakdawala, Linda, *Creating a Safer Perioperative Environment With an Obstructive Sleep Apnea Screening Tool*, Journal of PeriAnesthesia Nursing, vol. 26, No. 1 Feb. 2001, 15-24 (10 pages).
Lee, Chul Hee, et al., *Changes in Site of Obstruction in Obstructive Sleep Apnea Patients According to Sleep Position: A DISE Study*, Laryngoscope 00: Month 2014 (7 pages).

(56) References Cited

OTHER PUBLICATIONS

Lee, Jung Bok, et al., *Determining Optimal Sleep Position in Patients with Positional Sleep-Disordered Breathing Using Response Surface Analysis*, J. Sleep Res. (2009) 18, 26-35 (10 pages).
Lockhart, Ellen M., et al. *Obstructive Sleep Apnea Screening and Postoperative Mortality in a Large Surgical Cohort*, Sleep Medicine 14 (2013) 407-415 (9 pages).
Lynn, Lawrence A. and J. Paul Curry, *Patterns of Unexpected In-Hospital Deaths: A Root Cause Analysis*, Patient Safety in Surgery 2011, 5:3 (25 pages).
Mador, M. Jeffrey, et al., *Are the Adverse Effects of Body Position in Patients with Obstructive Sleep Apnea Dependent on Sleep Stage?*, Sleep Breath (2010) 14:13-17 (7 pages).
Mador, M. Jeffrey, et al., *Prevalence of Positional Sleep Apnea in Patients Undergoing Polysomnography*, Chest 2005; 128:2130-2137 (8 pages).
Marcus, Howard, *Obesity and Postoperative Surgical Risk*, The Doctors Company, Third Quarter 2010, 1-8 (8 pages).
Martin-Du Pan, Rémy, et al., *The Role of Body Position and Gravity in the Symptoms and Treatment of Various Medical Diseases*, Swiss Med. Wkly. 2004: 134:543-551 (10 pages).
Memtsoudis, Stavros G., et al., *A Rude Awakening—The Perioperative Sleep Apnea Epidemic*, N Engl. J. Med. 368:25, 2352-2353 (Jun. 20, 2013) (2 pages).
Menon, Akshay and Manoj Kumar, *Influence of Body Position on Severity of Obstructive Sleep Apnea: A Systematic Review*, Otolaryngology, vol. 2013, Article ID 670381 (2013) (8 pages).
Mininni, Nicolette C., et al., *Pulse Oximetry: An Essential Tool for the Busy Med-Surg Nurse*, American Nurse Today, Nov./Dec. 2009, 31-33 (3 pages).
Mokhlesi, Babak, *Empiric Postoperative Autotitrating Positive Airway Pressure Therapy / Generating Evidence in the Perioperative Care of Patients at Risk for Obstructive Sleep Apnea*, Chest 144/1 (Jul. 2013) 5-7 (3 pages).
Mull, Yvonne and Marshall Bedder, *Obstructive Sleep Apnea Syndrome in Ambulatory Surgical Patients*, AORN Journal, vol. 76, No. 3, 458-462 (Sep. 2002) (5 pages).
Nader, Nizar Z., et al., *Newly Identified Obstructive Sleep Apnea in Hospitalized Patients: Analysis of an Evaluation and Treatment Strategy*, Journal of Sleep Medicine, vol. 2, No. 4, 2006, 431-437 (7 Pages).
Pevernagie, Dirk A., et al., *Effects of Body Position on the Upper Airway of Patients with Obstructive Sleep Apnea*, Am J Respir Crit Care Med, vol. 152, 179-185, 1995 (7 pages).
Qureshi, Asher and Robert D. Ballard, *Obstructive Sleep Apnea*, J Allergy Clin Immunol, vol. 112, No. 4, 643-651 (2003) (9 pages).
Richard, Wietske, et al., *The Role of Sleep Position in Obstructive Sleep Apnea Syndrome*, Eur Arch Otorhinolaryngol (2006) 263:946-950 (5 pages).
Rocke, Daniel, et al., *Effectiveness of a Postoperative Disposition Protocol for Sleep Apnea Surgery*, American Journal of Otolaryngology—Head and Neck Medicine and Surgery 34 (2013) 273-277 (5 pages).
Gabbott, D.A., *The Effect of Single-Handed Cricoid Pressure on Neck Movement After Applying Manual In-Line Stabilisation*, Anaesthesia, 1997, 52, 586-602 (17 pages).
Ross, Jacqueline, *Obstructive Sleep Apnea: Knowledge to Improve Patient Outcomes*, Journal of PeriAnesthesia Nursing, vol. 23, No. 4 Aug. 2008, 273-275 (3 pages).
Setaro, Jill, *Obstructive Sleep Apnea: A Standard of Care That Works*, Journal of PeriAnesthesia Nursing, vol. 27, No. 5 Oct. 2012, 323-328 (6 pages).
Sheldon, Alison, et al., *Nursing Assessment of Obstructive Sleep Apnea in Hospitalised Adults: A Review of Risk Factors and Screening Tools*, Contemporary Nurse, vol. 34, Issue 1, Dec. 2009/Jan. 2010, 19-33 (16 pages).
Skinner, Margot A., et al., *Efficacy of the 'Tennis Ball Technique' Versus nCPAP in the Management of Position-Dependent Obstructive Sleep Apnoea Syndrome*, Respirology (2008) 13, 708-715 (8 pages).

Stearns, Joshua D. and Tracey L. Stierer, *Peri-Operative Identification of Patients at Risk for Obstructive Sleep Apnea*, Seminars in Anesthesia, Perioperative Medicine and Pain (2007) 26, 73-82 (10 pages).
Van Kesteren, Ellen R., et al., *Quantitative Effects of Trunk and Head Position on the Apnea Hypopnea Index in Obstructive Sleep Apnea*, Sleep, vol. 34, No. 8 (2011), 1075-1081 (7 pages).
Veasey, Sigrid C., et al., *Medical Therapy for Obstructive Sleep Apnea: A Review by the Medical Therapy for Obstructive Sleep Apnea Task Force of the Standards of Practice Committee of the American Academy of Sleep Medicine*, Sleep, vol. 29, No. 8 (2006), 1036-1044 (9 pages).
Wolfson, Alexander, et al., *Postoperative Analgesia for Patients with Obstructive Sleep Apnea Syndrome*, Seminars in Anesthesia, Perioperative Medicine and Pain (2007), 26, 103-109 (7 pages).
Yantis, Mary Ann, *Decreasing Surgical Risks for Patients with Obstructive Sleep Apnea*, AORN Journal, vol. 68, No. 1 (Jul. 1998), 50-55 (6 pages).
Ravesloot, M.J.L., and N. de Vries, *Reliable Calculation of the Efficacy of Non-Surgical Treatment of Obstructive Sleep Apnea Revisted*, Sleep, vol. 34, No. 1 (2011), 105-110 (6 pages).
Moon, Il Joon, et al., *Sleep Magnetic Resonance Imagine as a New Diagnostic Method in Obstructive Sleep Apnea Syndrome*, Laryngoscope 120: Dec. 2010, 2546-2554 (9 pages).
Nepomnayshy, Dmitry, et al., *Sleep Apnea: Is Routine Preoperative Screening Necessary?*, OBES Surg (2013) 23:287-192 (5 pages).
Press Release: *World's Leading Health Media Promotes Disinformation on Best Sleeping Positions* (Sep. 22, 2010), Sleeping Positions Research Summary (24 Studies), http://www.normalbreathing.com/l-6-best-sleep-positions.php (14 pages).
Oksenberg, Arie, et al., *Association of Body Position with Severity of Apneic Events in Patients with Severe Nonpositional Obstructive Sleep Apnea*, Chest 2000; 118; 1018-1024 (9 pages).
Oksenberg, Arie, *The Avoidance of the Supine Posture during Sleep for Patients with Supine-related Sleep Apnea*, BSM Protocols for Adherence and Treatment of Intrinsic Sleep Disorders, Chapter 23, 223-236 (14 pages).
Oksenberg, Arie and Donald Silverberg, *The Effect of Body Posture on Sleep-Related Breathing Disorders: Facts and Therapeutic Implications*, Sleep Medicine Reviews, vol. 2, No. 3, 139-162 (1998) (25 pages).
Oksenberg, Arie, et al., *Positional Therapy for Obstructive Sleep Apnea Patients: A 6-Month Follow-Up Study*, Laryngoscope 116, Nov. 2006, 1995-2000 (6 pages).
Oksenberg, Arie, et al., *REM-Related Obstructive Sleep Apnea: The Effect of Body Position*, Journal of Clinical Sleep Medicine, vol. 6, No. 4 (2010), 343-348 (6 pages).
Ozeke, Ozcan, et al., *Influence of the Right-Versus Left-Sided Sleeping Position on the Apnea-Hypopnea Index in Patients with Sleep Apnea*, Sleep Breath, published online Jun. 16, 2011 (5 pages).
Ozeke, Ozcan, et al., *Sleep Apnea, Heart Failure, and Sleep Position*, Sleep Breath, published online Nov. 9, 2011 (4 pages).
Permut, Irene, et al., *Comparison of Positional Therapy to CPAP in Patients with Positional Obstructive Sleep Apnea*, Journal of Clinical Sleep Medicine, vol. 6, No. 3 (2010), 238-243 (6 pages).
Author Unknown, *Positioning of Surgical Patients With Sleep Apnea*, ClinicalTrials.gov, http://clinicaltrials.gov/ct2/show/NCT02123238?term-apnea+and+position&rank=3 (2014) (5 pages).
Author Unknown, *Obstructive Sleep Apnea May Block the Path to a Positive Postoperative Outcome*, 2007 Pennsylvania Patient Safety Authority, reprinted from the PA-PSRS Patient Safety Advisory, vol. 4, No. 3 (Sep. 2007) (9 pages).
Proczko, Monika, et al., *Stop-Bang and the Effect on Patient Outcome and Length of Hospital Stay when Patients are not Using Continuous Positive Airway Pressure*, J Anesth, published online May 29, 2014 (7 pages).
Ramachandran, Satya Krishna, et al., *Derivation and Validation of a Simple Perioperative Sleep Apnea Prediction Score*, Society for Ambulatory Anesthesiology, vol. 110, No. 4 (Apr. 2010), 1007-1015 (9 pages).
Ravesloot, M.J.L. and N. de Vries, *Calculation of Surgical and Non-Surgical Efficacy for OSA / Reliable Calculation of the Efficacy*

(56) References Cited

OTHER PUBLICATIONS of Non-Surgical and Surgical Treatment of Obstructive Sleep Apnea Revisted, vol. 34, Issue 01 (2001) 105-110 (2 pages).
Ravesloot, M.J.L., et al., *The Undervalued Potential of Positional Therapy in Position-Dependent Snoring and Obstructive Sleep Apnea—A Review of the Literature*, Sleep Breath, published online Mar. 24, 2012 (11 pages).
Ravesloot, Madeline J.L., et al., *Treatment Adherence Should be Taken into Account when Reporting Treatment Outcomes in Obstructive Sleep Apnea*, Sleep Medicine, vol. 124, Issue 1 (Jan. 2014) 344-345 (3 pages).
Richardson, Annette and Anne Killen, *How Long do Patients Spend Weaning from CPAP in Critical Care?*, Intensive and Critical Care Nursing (2006) 22, 206-213 (8 pages).
Rosenberg, Russell and Paul Doghramji, *Optimal Treatment of Obstructive Sleep Apnea and Excessive Sleepiness*, Springer Healthcare Communication, published online Apr. 3, 2009, 295-312 (18 pages).
Rosenthal, Leon, *Got CPAP? Use it in the Hospital!*, Sleep Breath, published online Nov. 25, 2011 (4 pages).
Safiruddin, Faiza, et al., *Analysis of the Influence of Head Rotation During Drug-Induced Sleep Endoscopy in Obstructive Sleep Apnea*, Laryngoscope 124: Sep. 2014, 2195-2199 (5 pages).
Seet, Edwin and Frances Chung, *Obstructive Sleep Apnea: Preoperative Assessment*, Anesthesiology Clin 28 (2010) 199-215 (17 pages).
Seet, Edwin, et al., *Perioperative Clinical Pathways to Manage Sleep-Disordered Breathing*, Sleep Med Clin 8 (2013) 105-120 (16 pages).
Sforza, Emilia, et al., *A 3-Year Longitudinal Study of Sleep Disordered Breathing in the Elderly*, European Respiratory Journal, vol. 40, No. 3 (2012) 665-672 (8 pages).
Sforza, E., et al., *Natural Evolution of Sleep Apnoea Syndrome: A Five Year Longitudinal Study*, European Respiratory Journal, 1994, 7, 1765-1770 (6 pages).
Shafazand, Shirin, *Perioperative Management of Obstructive Sleep Apnea: Ready for Prime Time?*, Cleveland Clinic Journal of Medicine, vol. 76, Supp. 4, Nov. 2009 (6 pages).
Siddiqui, Fouzia, et al. *Half of Patients with Obstructive Sleep Apnea have a Higher NREM AHI than REM AHI*, Sleep Medicine 7 (2006) 281-285 (5 pages).
Singh, M., et al., *Proportion of Surgical Patients with Undiagnosed Obstructive Sleep Apnoea*, British Journal of Anaesthesia 110 (4); 629-636 (2013) (8 pages).
Skinner, Margot A., et al., *Elevated Posture for the Management of Obstructive Sleep Apnea*, Sleep and Breathing, vol. 8, No. 4 (2004) 193-200 (10 pages).
Author Unknown, *There's More than One Way to Improve Nightime Breathing*, European Sleep Works, http://www.sleepworks.com/resource/medical-needs/sleep-apnea (2014) (3 pages).
Park, Steven V., *Sleep Apnea CPAP Compliance Craziness*, Doctor Steven Y_ Park, MD New York, NY Integrative Solutions for Obstructive Sleep Apnea, Upper Airway Resistance Syndrome, and Snoring (Nov. 10, 2009) (7 pages).
Monk, Timothy H., et al., *Measuring Sleep Habits Without Using a Diary: The Sleep Timing Questionnaire*, Sleep, vol. 26, No. 2 (2003) 208-212 (5 pages).
Sorscher, Adam J. and Evan M. Caruso, *Frequency of Provision of CPAP in the Inpatient Setting: An Observational Study*, Sleep Breath, published online Nov. 23, 2011 (6 pages).
Spurr, Kathy F., et al., *Prevalence of Unspecified Sleep Apnea and the use of Continuous Positive Airway Pressure in Hospitalized Patients, 2004 National Hospital Discharge Survey*, Sleep Breath (2008) 12:229-234 (8 pages).
Srijithesh PR, et al., *Positional Therapy for Obstructive Sleep Apnoea (Protocol)*, The Cochrane Library 2014, Issue 2 (11 pages).
Sundar, Eswar, et al., *Perioperative Screening for the Management of Patients with Obstructive Sleep Apnea*, JCOM, vol. 18, No. 9, Sep. 2011, 399-411 (13 pages).

Szollosi, Irene, et al., *Lateral Sleeping Position Reduces Severity of Central Sleep Apnea/Cheyne-Stokes Respiration*, Sleep, vol. 29, No. 8 (2006), 1045-1051 (7 pages).
Author Unknown, *A Promising Concept of Combination Therapy for Positional Obstructive Sleep Apnea*, Springer Link, http://link.springer.com/article/10.1007/s11325-014-1068-8, Oct. 2014 (4 pages).
Author Unknown, *Upper Airway Collapse During Drug Induced Sleep Endoscopy: Head Rotation in Supine Position Compared with Lateral Head and Truck Position*, Springer Link, http://link.springer.com/article/10.1007/s00405-014-3215-z, Aug. 2014 (4 pages).
Vasu, Tajender S., et al., *Obstructive Sleep Apnea Syndrome and Postoperative Complications*, Arch Otolaryngol Head Neck Surg, vol. 136, No. 10, Oct. 2010 (5 pages).
Matthews, Dan, *Mattresses—A Futile Weapon in the Fight Against Sleep Apnea*, http://www.danmatthewsdds.com/mattresses-%E2%80%93-futile-weapon-fight-sleep-apnea/ (2014) (1 page).
Marks, Steve, *Hospital Care of Patients with Sleep Apnea*, Areté Sleep Health, last modified on May 16, 2013 (63 pages).
Carlisle, Heather, *The Case for Capnography in Patients Receiving Opioids*, American Nurse Today, vol. 9, No. 9 (Sep. 2014) 22-27 (69 pages).
Gold, Jenny, *The Sleep Apnea Business Is Booming, and Insurers Aren't Happy*, NPR_ApnesvsInsurres.mht, (Jan. 16, 2012) (3 page).
Author unknown, *Sleep right, Sleep tight, Natural sleep before medicines*, Sleep Diary, www.nps.org.au/sleep, last modified Jul. 7, 2010 (4 pages).
Quan, S. F., *Evolution of OSA*, Thorax 1998; 53:532 (4 pages).
Maurer, J. T., et al., *Treatment of Obstructive Sleep Apnea with a New Vest Preventing the Supine Position*, Thieme-Connect (2003) (1 page).
Schreuder, K.E., *The Effect of Cervical Positioning on Benign Snoring by Means of a Custom-Fitted Pillow*, Centre for Sleep and Wake Disorders Kempenhaeghe, 5591 Ve Heeze, the Netherlands, last modified Dec. 1, 2011 (4 pages).
Chung, Frances, *Semi-up Right Position Study*, Clinical Trials.gov, last updated May 28, 2014 (5 pages).
Author Unknown, *National Sleep Foundation Sleep Diary, National Sleep Foundation*, last modified Apr. 18, 2003 (2 pages).
Takaoka, Shanon, CPAP Adherence, Is it too much "pressure"?, Feb. 7, 2007 (41 pages).
Seren, Suaf, *The Effect of Pure Prone Positioning Therapy for the Patients With Mild to Moderate Obstructive Sleep Apnea*, ClinicalTrials.gov, last updated Jun. 7, 2011 (4 pages).
Jackman, Shawn M. and Bruce Hubbert, *Riding the Wireless Wave (without wiping out)*, HIMSS12 Annual Conference & Exhibition, last modified Feb. 20, 2012 (133 pages).
De Vries, Nico and Madeline Ravesloot, *Apnea Calculator*, http://apneacalculator.com (2014) (2 pages).
Oexman, Robert, *Can a Mattress Really Impact Your Sleep?*, Huffpost Healthy Living, Posted Oct. 14, 2012, 10:00 a.m. (8 pages).
Palmer, Laura and Suzanne R. Morrison, *Obesity and Obstructive Sleep Apnea / Is there a limit for ambulatory surgery?*, OR Nurse Journal, Sep. 2014 (9 pages).
Oksenberg, Arie, *Are We Missing a Simple Treatment for Most Adults Sleep Apnea Patients? The Avoidance of the Supine Sleep Position*, ResearchGate.net, Aug. 12, 2014 (2 pages).
Author Unknown, *Obstructive Sleep Apnea (OSA), Care of Adult Patients*, St. Anthony Central Hospital Clinical Standards, Jul. 8, 2009 (9 pages).
Gross, Jeffrey B., *Practice Guidelines for the Perioperative Management of Patients with Obstructive Sleep Apnea: An Updated Report by the American Society of Anesthesiologists Task Force on Perioperative Management of Patients with Obstructive Sleep Apnea*, U.S. Department of Health & Human Services, updated on May 9, 2014 (13 pages).
O'Connor, Anahad, *Treating Sleep Apnea Without the Mask*, NYTimes.com, Apr. 9, 2012 (7 pages).
Stradling, J. R. and R. J. O. Davies, *Sleep 1: Obstructive Sleep Apnea/Hypopnoea Syndrome: Definitions, Epidemiology, and Natural History*, Thorax 2004;59:73-78 (6 pages).

(56) References Cited

OTHER PUBLICATIONS

Pyke, Josh, et al, *Continuous Pulse Oximetry Monitoring in the Inpatient Population*, Patient Safety & Quality Healthcare, May/Jun. 2009 (5 pages).

EP Search Report for Application No. EP 13 79 3571, dated Sep. 8, 2015 (9 pages).

Service Manual—"TotalCare® Bed System" from Hill-Rom, Product No. P1900, MAN112 Rev 7, by Hill-Rom Services, Inc. (2007) (1105 pages).

User Manual—"TotalCare® Bed System" from Hill-Rom, Product No. P1900, USR042 REV11, by Hill-Rom Services, Inc. (2007) (112 pages).

SleepEducation-Blog, "Positional therapy harness helps reduce sleep apnea for some," www.sleepeducation.com, posted Friday, Jun. 18, 2010 (7 pages).

SPANAmerica: PressureGuard® TurnSelect®, www.archive.org/web/20090201172625/http://spanamerica.com/turn_select.php; Aug. 18, 2014 (2 pages).

PCT Search Report and Written Opinion for PCT/US2014/18033, completed Aug. 18, 2014.

PCT Search Report for PCT/US2013/042313, completed Dec. 6, 2013.

EP Search Report for Application No. 15180086.9-1651, dated Dec. 22, 2015, 7 pages.

Japanese Office Action for Japanese Patent Application No. 2017-073542 dated Feb. 7, 2018 and its English translation; 11 pages total.

Japanese Patent Application Publication No. JP 2011-143237A dated Jul. 28, 2011 and its machine-generated English translation; 34 pages total.

PCT Patent Application Publication No. WO 2013/031504 A1 published on Mar. 7, 2018 and the English translation of the Abstract only; 63 pages total.

\* cited by examiner

LAYERED GRADUATED LATERAL ROTATION APPARATUS

CROSS-REFERENCE TO RELATED APPLICATIONS

This application claims priority to U.S. Provisional Patent Application Ser. No. 62/531981, filed Jul. 13, 2017 and titled "LAYERED GRADUATED LATERAL ROTATION APPARATUS," which is herein incorporated by reference in its entirety.

BACKGROUND

The subject matter disclosed herein relates generally to adverse event mitigation devices, systems, and methods and, more particularly, but not exclusively, to devices, systems, and methods for the prevention and treatment of sleep apnea. These devices, systems, and methods may include an active intervention, a passive intervention, or a continuous intervention. The embodiments described herein may also be effective in reducing snoring.

While various adverse event mitigation devices, systems, and methods have been developed, there is still room for improvement. Thus, a need persists for further contributions in this area of technology.

SUMMARY

The present disclosure includes one or more of the features recited in the appended claims and/or the following features which, alone or in any combination, may comprise patentable subject matter.

In one aspect, a lateral rotation apparatus includes a person support surface having head, torso and leg segments each having an independently rotatable person support plane. A wedge is positioned below the person support surface. The wedge is operable to rotate the head segment of the person support surface to a head tilt angle approximately at a centerline of the head segment in the range of about 7° to about 30° relative to a horizontal support plane. The wedge is also operable to rotate the torso segment of the person support surface to a torso tilt angle approximately at a centerline of the torso segment that is within a range of about 5° to about 10° less than the head tilt angle. The wedge provides a graduated lateral rotation of the person support surface.

In some embodiments, the wedge includes a corner. A first sidewall extends in a first direction from the corner. A second sidewall extends in a second direction from the corner. The first sidewall is substantially perpendicular to the second sidewall. A thickness of the wedge is greater at the corner than a thickness of the wedge at an end of the first sidewall. In some embodiments, the thickness of the wedge gradually decreases from the corner to the end of the first sidewall. In some embodiments, a thickness of the wedge is greater at the corner than a thickness of the wedge at an end of the second sidewall. In some embodiments, the thickness of the wedge gradually decreases from the corner to the end of the second sidewall.

In some embodiments, the wedge includes a plurality of layers stacked on one another. In some embodiments, each of the plurality of layers has a different area. In some embodiments, a bottom layer has a greater area than an area of a top layer positioned on the bottom layer. In some embodiments, the bottom layer includes a first sidewall and the top layer includes a first sidewall that is coplanar with the first sidewall of the bottom layer. The first sidewall of the bottom layer is longer than the first sidewall of the top layer. In some embodiments, the bottom layer includes a second sidewall and the top layer includes a second sidewall that is coplanar with the second sidewall of the bottom layer. The second sidewall of the bottom layer is longer than the second sidewall of the top layer. In some embodiments, the first sidewall of the bottom layer is substantially perpendicular to the second sidewall of the bottom layer, and the first sidewall of the top layer is substantially perpendicular to the second sidewall of the top layer.

In some embodiments, the bottom layer further includes an angled sidewall connecting ends of the first sidewall and the second sidewall of the bottom layer. The top layer includes an angled sidewall connecting ends of the first sidewall and the second sidewall of the top layer. In some embodiments, the angled sidewall of the bottom layer is not coplanar with the angled sidewall of the top layer. In some embodiments, the wedge includes a corner where the first sidewall and the second sidewall of the bottom layer meet and the first sidewall and the second sidewall of the top layer meet. The angled sidewall of the bottom layer is positioned a further distance from the corner than the angled sidewall of the top layer.

In some embodiments, the torso segment is rotated to a torso tilt angle approximately at a centerline of the torso segment in the range of about 0° to about 25°.

In some embodiments, the head segment is rotated to a head tilt angle approximately at a centerline of the head segment in the range of about 10° to about 15°. In such an embodiment, the torso segment is rotated to a torso tilt angle approximately at a centerline of the torso segment in the range of about 5° to about 10°. In some embodiments, the leg segment is rotated to a leg tilt angle approximately at a centerline of the leg segment in the range of about 0° to about 5°.

In some embodiments, the person support surface includes a support material having a density. The head tilt angle is a function of the density of the support material. In some embodiments, the torso tilt angle is a function of the density of the support material.

In another aspect, a lateral rotation apparatus includes a wedge positioned below a person support surface having head, torso and leg segments each having an independently rotatable person support plane. The wedge includes a plurality of layers stacked on one another. Each of the plurality of layers has a different area. The wedge is operable to rotate the head segment of the person support surface to a head tilt angle approximately at a centerline of the head segment in the range of about 7° to about 30° relative to a horizontal support plane. The wedge is also operable to rotate the torso segment of the person support surface to a torso tilt angle approximately at a centerline of the torso segment that is within a range of about 5° to about 10° less than the head tilt angle. The wedge provides a graduated lateral rotation of the person support surface.

In some embodiments, the wedge includes a corner. A first sidewall extends in a first direction from the corner. A second sidewall extends in a second direction from the corner. The first sidewall is substantially perpendicular to the second sidewall. A thickness of the wedge is greater at the corner than a thickness of the wedge at an end of the first sidewall. In some embodiments, the thickness of the wedge gradually decreases from the corner to the end of the first sidewall. In some embodiments, a thickness of the wedge is greater at the corner than a thickness of the wedge at an end of the second sidewall. In some embodiments, the thickness of the wedge gradually decreases from the corner to the end of the second sidewall.

In some embodiments, a bottom layer has a greater area than an area of a top layer positioned on the bottom layer. In some embodiments, the bottom layer includes a first sidewall and the top layer includes a first sidewall that is coplanar with the first sidewall of the bottom layer. The first sidewall of the bottom layer is longer than the first sidewall of the top layer. In some embodiments, the bottom layer includes a second sidewall and the top layer includes a second sidewall that is coplanar with the second sidewall of the bottom layer. The second sidewall of the bottom layer is longer than the second sidewall of the top layer. In some embodiments, the first sidewall of the bottom layer is substantially perpendicular to the second sidewall of the bottom layer. The first sidewall of the top layer is substantially perpendicular to the second sidewall of the top layer.

In some embodiments, the bottom layer includes an angled sidewall connecting ends of the first sidewall and the second sidewall of the bottom layer. The top layer includes an angled sidewall connecting ends of the first sidewall and the second sidewall of the top layer. In some embodiments, the angled sidewall of the bottom layer is not coplanar with the angled sidewall of the top layer.

In some embodiments, the wedge includes a corner where the first sidewall and the second sidewall of the bottom layer meet and the first sidewall and the second sidewall of the top layer meet. The angled sidewall of the bottom layer is positioned a further distance from the corner than the angled sidewall of the top layer.

In some embodiments, the torso segment is rotated to a torso tilt angle approximately at a centerline of the torso segment in the range of about 0° to about 25°.

In some embodiments, the head segment is rotated to a head tilt angle approximately at a centerline of the head segment in the range of about 10° to about 15°. In such an embodiment, the torso segment is rotated to a torso tilt angle approximately at a centerline of the torso segment in the range of about 5° to about 10°. In some embodiments, the leg segment is rotated to a leg tilt angle approximately at a centerline of the leg segment in the range of about 0° to about 5°.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
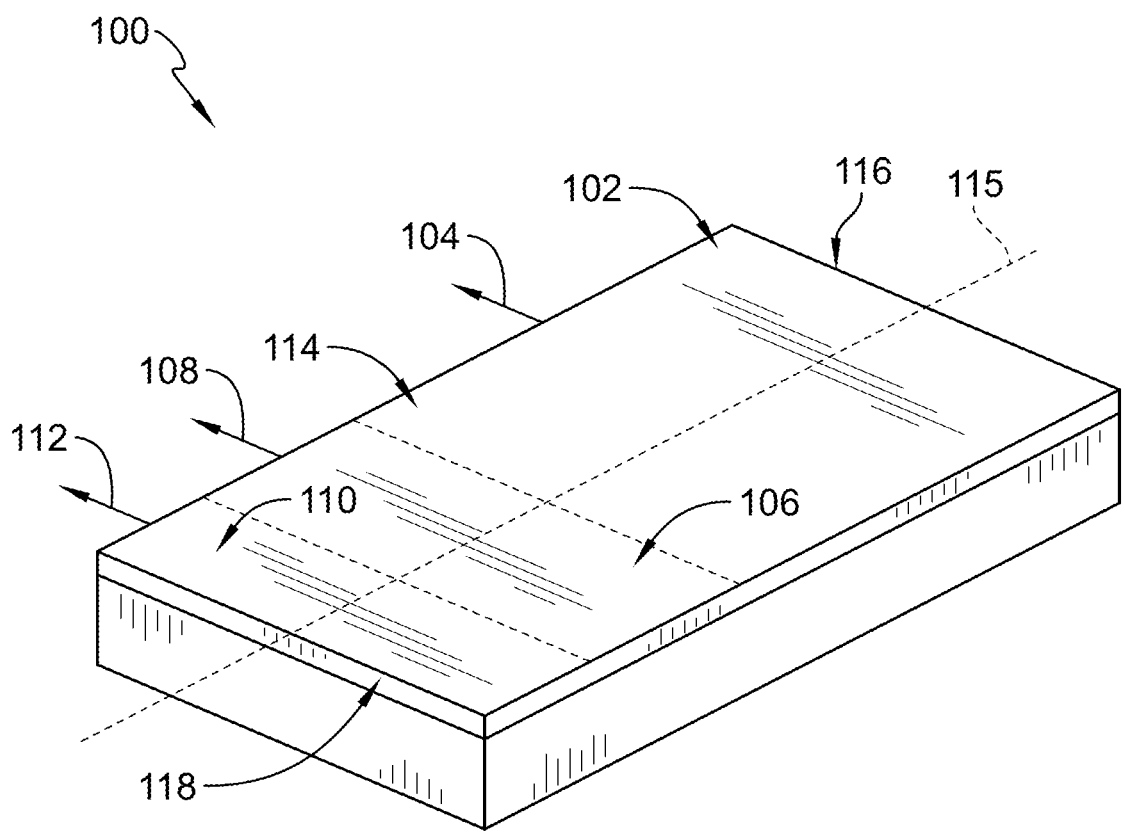
FIG. 1 is a perspective view from a top of a sleep surface illustrated as a mattress.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

The embodiments described herein relate to devices, systems and methods to reduce the occurrence and/or duration of or prevent sleep apnea events and/or snoring. The embodiments demonstrate efficacy in preventing mild to moderate obstructive sleep apnea, with improved tolerability relative to current therapy (i.e., CPAP).

The described devices, systems and methods are not limited to the specific embodiments described herein. In addition, components of each device, system and/or steps of each method may be practiced independent and separate from other components and method steps, respectively, described herein. Each component and method also can be used in combination with other systems and methods.

Referring to FIGS. 1-6, a support system 100 includes a support surface having one or more support sections that are angled to form a lateral support plane that prevents or restricts the user from sleeping in a supine position, and, more specifically, reduces a time duration that the user sleeps with his/her upper respiratory tract oriented vertically or at an undesirable lateral rotational angle with respect to a vertical plane substantially perpendicular to a horizontal plane of the support surface. In certain embodiments, the lateral rotational angle of the user's head with respect to the vertical plane is at least 30 degrees and, more specifically, at least 45 degrees. In an alternative embodiment, the lateral rotational angle of the user's head with respect to the vertical plane may be less than 30 degrees. In one embodiment, the support sections provide multiple support planes for supporting the user's body.

In one embodiment as shown in FIG. 1, a support system 100 suitable for supporting a user, such as a person, for example, includes plurality of support sections, namely a first or leg support section 102 forming a first support plane 104, a second or torso support section 106 forming a second support plane 108, and a third or head support section 110 forming a third support plane 112 that collectively define a multi-plane, sleep surface 114 that may be progressively angled along a longitudinal axis 115 of support system 100, from a first or bottom edge 116 of sleep surface 114 to an opposing second or top edge 118 of sleep surface 114, resulting in relatively greater rotation of the upper respiratory tract of the user (as necessary for efficacy in preventing obstructive apnea) and relatively lesser rotation in the lower body of the user (resulting in greater comfort and perceived stability by avoiding rotation of a majority of the user's body mass).

Unlike conventional positional therapies for the prevention of obstructive sleep apnea, which attempt to manipulate the user's sleep position and/or orientation using rotation of one plane, in certain embodiments the system described herein uses multiple support planes formed by one or more support sections to laterally rotate the user. For example, in one embodiment, two support sections provide two separate support planes, with a first support plane defined by the first support section configured to support the torso and the legs of the user, and a second support plane defined by the second support section configured to support the neck and the head of the user.

In an alternative embodiment, three support sections provide three separate support planes, with a first support plane defined by the first support section configured to support the legs of the user, a second support plane defined by the second support section configured to support the torso of the user, and a third support plane defined by the third support section configured to support the head of the user.

In a further alternative embodiment, more than three support sections, for example, numerous independent support sections having a length in a longitudinal direction of sleep surface 114 of 2-18 inches or, more specifically, 4-12 inches, or, even more specifically, 6 inches, provide a corresponding number of separate support planes. Each support section can be laterally rotated independently of other support sections to collectively form sleep surface 114. In a particular embodiment, the numerous support sections can be combined to form separate support sections, for example, creating a first support section having a length of 18 inches in the longitudinal direction at the foot of the support surface, an adjacent second support section having a length of 12 inches in the longitudinal direction, and a third support section adjacent the second support section having a length in the longitudinal direction of 6 inches. In these embodiments, the support sections forming the support planes can be rotated as necessary or desired to achieve an optimal configuration that is clinically effective (i.e., prevents apnea) and demonstrates acceptable tolerance (i.e., allows the user to sleep comfortably). In an alternative embodiment, a continuously sloped sleep surface is formed by a plurality of support sections without step increases in lateral rotational angle; this is illustrated as a sleep surface with an infinite number of support sections.

In the embodiments described herein, the length in the longitudinal direction of each support section and defined support plane (and the resulting location of transitions between support planes) is designed to achieve clinical efficacy and tolerability. Therefore, a specific length can be defined in a number of configurations, including without limitations: (a) generic plane dimensions (e.g., based on average body geometry, a length of a torso section of the user defined so that when an average user's head is supported by a head support section, a transition between the torso support section and the leg support section occurs below the user's S3 vertebrae); (b) customized plane dimensions (e.g., a torso support plane has a suitable length in the longitudinal direction appropriate to the user's leg length, torso length, and/or a distance from the user's shoulder to his/her inseam); or (c) dynamic plane dimensions (e.g., transitions selected on dynamic surface appropriate to user, selection being either user-selected, care-giver defined, or automatically calculated).

Figure 2:
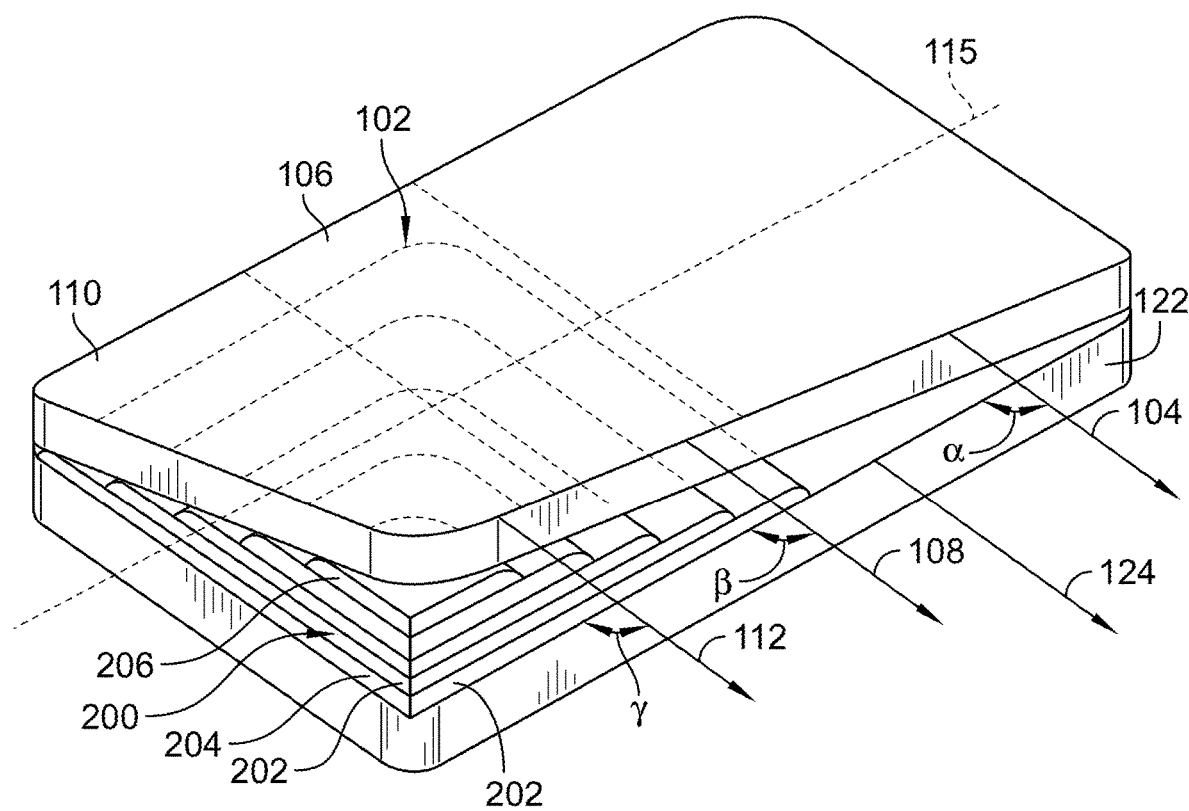
FIG. 2 is a perspective view from the top of the sleep surface of a lateral rotation apparatus in accordance with an embodiment and positioned between the sleep surface shown in FIG. 1 and a horizontal support surface illustrated as a box spring.
Figure 3:
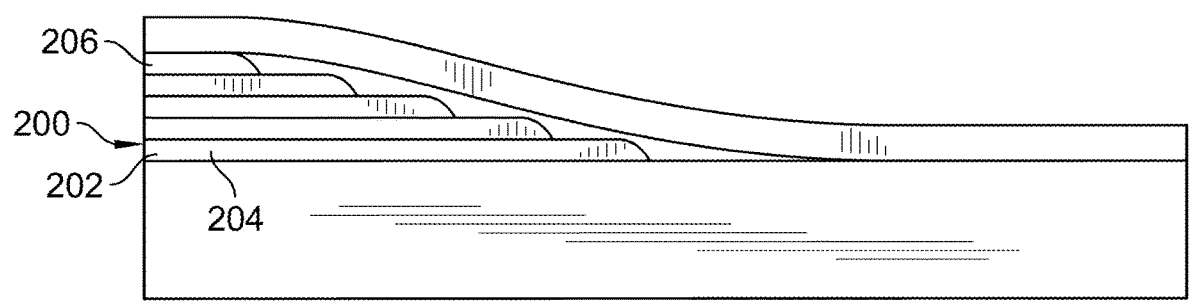
FIG. 3 is a side view of the sleep surface of FIG. 2 on the lateral rotation apparatus and positioned between the sleep surface shown in FIG. 1 and a horizontal support surface illustrated as a box spring.
Figure 4:
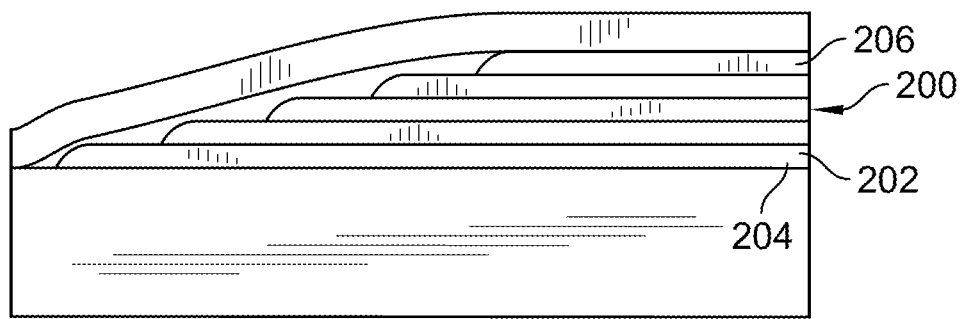
FIG. 4 is a head view of the sleep surface of FIG. 2 on the lateral rotation apparatus and positioned between the sleep surface shown in FIG. 1 and a horizontal support surface illustrated as a box spring.

Referring to FIGS. 2-4, a lateral rotation apparatus 200 is provided in the form of a wedge positioned between the support system 100 and a horizontal support surface 122 forming a horizontal support plane 124 to provide a gradual lateral rotation of the support system 100. In one embodiment, the support system 100 is a mattress, wherein each of the support sections 102, 106, 110 are integrally formed. Alternatively, the support sections 102, 106, 110 may be separately formed. In yet another embodiment, only some of the support sections 102, 106, 110 may be integrally formed, for example support sections 102, 106 may be integrally formed or support sections 106, 110 may be integrally formed. The mattress may be any conventional mattress, i.e. spring mattress, pillow top mattress, foam mattress, air mattress, etc. or any suitable mattress utilized in a healthcare setting. The horizontal support plane 124 may be formed along a box spring, frame, or any other suitable device for retaining a mattress.

The lateral rotation apparatus 200 may be formed from foam, plastic, metal, or any other suitable material. The lateral rotation apparatus 200 includes a plurality of layers 202 stacked on top of one another. Each layer 202 may have a different density. For example, in one embodiment, a bottom layer 204 may have a greater density than a top layer 206. In one embodiment, the density of each layer 202 may decrease each layer 202 when moving from the bottom layer 204 to the top layer 206. In some embodiments, some of the layers 202 or all of the layers 202 may have the same density. The layers 202 may be all be formed from the same material. Alternatively, some layers 202 may be formed from different materials, for example materials having different densities.

In certain embodiments, the support sections 102, 106, 110 defining the corresponding support surface 104, 108, 112 rotate about an axis extending parallel with a longitudinal axis 115 of the support system. In particular, the lateral rotation apparatus 200 facilitates rotation of the support sections 102, 106, 110. The rotation of each support section 102, 106, 110 allows the caregiver or the user ability to focus on progressively increasing an angle of rotation in one or more support sections 102, 106, 110. In certain embodiments, a rotational angle at which the support plane 112 defined by the support section 110 is positioned is greater that a rotational angle of the support plane 108 defined by the support section 106, which is greater than a rotational angle at which the support plane 104 defined by the support section 102 is positioned.

In a particular embodiment, the first support plane 104 defined by the support section 102 configured to support the legs of the user is positioned at a rotational angle α approximately at a centerline of the first support section 102 of approximately 10° with respect to the horizontal support plane 124, the second support plane 108 defined by the second support section 106 configured to support the torso of the user is positioned at a rotational angle β of approximately 15° approximately at a centerline of the second support section 106 with respect to the horizontal support plane 124, and the third support plane 112 defined by the third support section 110 configured to support the head of the user is positioned at a rotational angle γ of approximately 20° approximately at a centerline of the third support section 110 with respect to the horizontal support plane 124. In alternative embodiments, the support planes 104, 108, 112 can be positioned at any suitable rotational angle including any suitable lateral rotational angle and/or any suitable longitudinal rotational angle. It should be noted that the measured rotation of the corresponding support section 102, 106, 110 is measured approximately at a centerline of the support section 102, 106, 110. A remainder of the support section 102, 106, 110 may have a different slope due to a weight of the support system 100, e.g. the mattress, a density of the support system 100, and/or a weight of an individual on the support surface. That is, the tilt angle within a particular support section 102, 106, 110 may vary throughout the support system 100. Generally, the lateral rotation apparatus 200 slopes the support system 100 such that gradual lateral rotation is achieved between the support sections 102, 106, and 110.

In a particular embodiment, first support section 102 defines support plane 104 positioned at a lateral rotational angle α of approximately 20° to approximately 30° approximately at a centerline of the first support section 102, or more specifically, approximately 20° to approximately 25°, or, even more specifically, approximately 25° with respect to the horizontal support plane 124. Second support section 106 defines support plane 108 positioned at a lateral rotational angle β of approximately 10° to approximately 20° approximately at a centerline of the second support section 106, or more specifically, approximately 10° to approximately 15°, or, even more specifically, approximately 15°, with respect to the horizontal support plane 124. Third support section 110 defines support surface 112 positioned at a lateral rotational angle γ of approximately 5° to approximately 15° approximately at a centerline of the third support section 110, or more specifically, approximately 10°, with respect to the horizontal support plane 124. Other lateral rotational angles and step increases in lateral rotational angles between each support section may also be used to achieve a progressive lateral rotational angle. In one embodiment, the lateral rotation apparatus 200 may rotate the head segment 110 to a head tilt angle in the range of about 7° to about 30° relative to the horizontal support plane 124. The lateral rotation apparatus 200 may also rotate the torso segment 106 to a torso tilt angle that is within a range of about 5° to about 10° less than the head tilt angle.

Each of first support section 102, second support section 106, and third support section 110 has a respective height in a direction perpendicular to longitudinal axis 115 of support system 100. In one embodiment, first support section 102 has a maximum height from the horizontal support plane 124 to support plane 116 in a direction perpendicular to longitudinal axis 115 of 14 to 18 inches approximately at a centerline of the first support section 102, or more specifically, 16 to 17 inches; second support section 106 has a maximum height from the horizontal support plane 124 to support plane 108 in a direction perpendicular to longitudinal axis 115 of 8 to 12 inches approximately at a centerline of the second support section 106, or more specifically, 9 to 10 inches; and third support section 110 has a maximum height from the horizontal support plane 124 to support plane 112 in a direction perpendicular to longitudinal axis 115 of 4 to 8 inches approximately at a centerline of the third support section 110, or more specifically, 6 to 7 inches. As a result, the support sections can be designed with desired heights and defining support planes positioned at desired rotational angles such that support surface 100 provides a composite longitudinal plane angle (e.g., reverse Trendelenburg angle), to facilitate the prevention and/or treatment of sleep apnea as well as to improve tolerability.

In one embodiment, each of support sections 102, 106, 110 are rotatable about longitudinal axis 115 to provide sleep surface 114 having a right side slope or, alternatively, a left side slope to allow the user to sleep on his/her right side or left side, respectively. In certain embodiments, support sections 102, 106, 110 are formed of more than one material, for example, two or more materials, such as two foam materials, having different densities, with the less dense material covering the denser material.

In this embodiment, lateral rotation apparatus 200 allows the user to sleep on either his/her right side or left side, based on the user's sleeping preference, and based on how the lateral support apparatus 200 is rotated on the horizontal support surface 122. This sleeping preference may not be static. For example, if the user has an injury, an ache, or a desire to change his/her sleeping preference, the orientation of lateral rotation apparatus 200 can be changed at any time to accommodate the user's sleeping preference. The orientation can be changed from day to day or during the night. Moreover, from a manufacturing standpoint, a versatile lateral rotation apparatus 200 prevents having to manufacture and distribute a lateral rotation apparatus 200 having a right side slope and a separate lateral rotation apparatus 200 having a left side slope, which would increase production and distribution costs. Finally, a potential purchaser would not have to commit to a sleep side before purchasing the product, which might be a deterrent to purchasing the product.

Lateral rotation apparatus 200 is customizable to anthropometric dimensions of the individual user to facilitate support surface performance that optimizes or matches the design intent—the body position of the user will prevent or limit undesirable sleep apnea episodes and provide improved comfort. As illustrated in FIGS. 3 and 4, the support sections 102, 106, 110 are not sloped evenly, e.g. the support sections 102, 106, 110 do not slope in a straight line. Rather the support sections 102, 106, 110 slope at different angles when sloping from head to foot or side to side.

Figure 5:
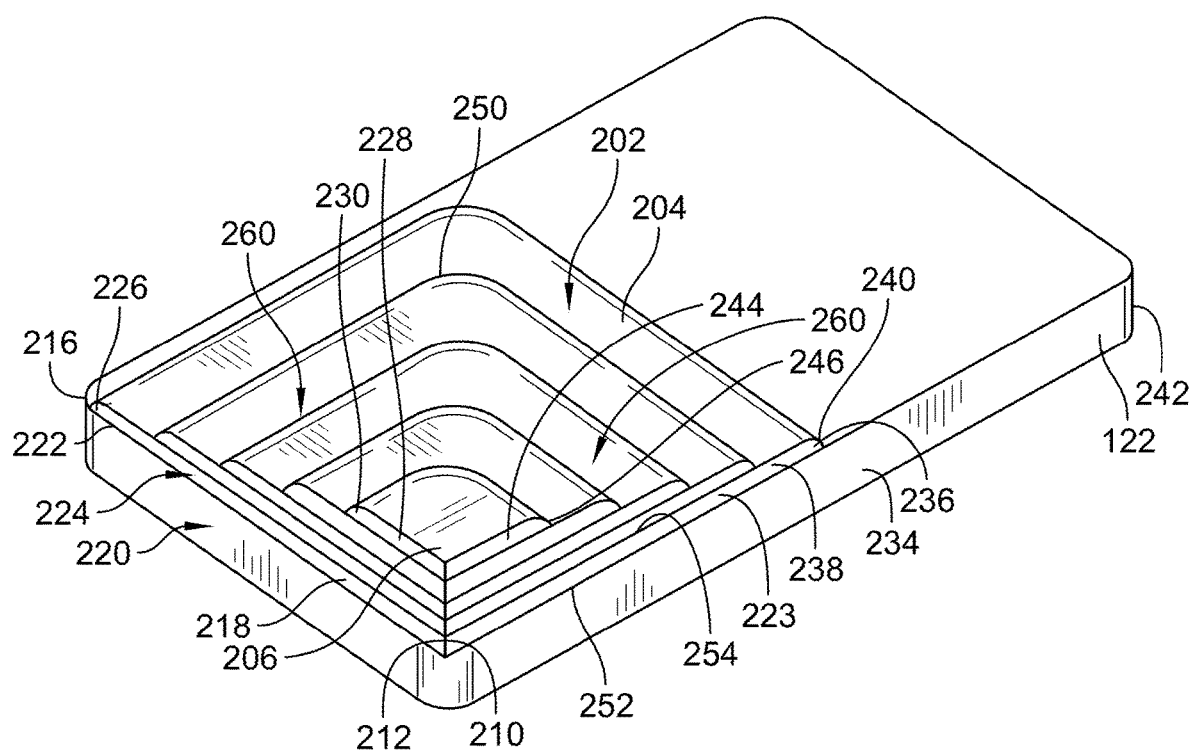
FIG. 5 is perspective view from the top of the horizontal support surface of the lateral rotation apparatus shown in FIG. 2.

Referring to FIG. 5, the lateral rotation apparatus 200 is formed from the plurality of layers 202, wherein each of the plurality of layers 202 has a different area. The bottom layer 204 has an area that is greater than the area of the next layer 202 in the stack of layers 202. When moving from the bottom layer 204 to the top layer 206, each layer 202 has an area that is smaller than the area of the layer 202 positioned below. Accordingly, the bottom layer 204 has the greatest area and the top layer 206 has the smallest area. Each layer 202 includes a corner 210, wherein, in the illustrative embodiment, the corner 210 of each layer 202 is aligned to form a corner 212 of the lateral rotation apparatus 200. The corner 212 of the lateral rotation apparatus 200 is positioned at a corner 214 of the horizontal support surface 122. As illustrated in FIGS. 3 and 4, the corner 212 extends vertically from and substantially parallel to the horizontal support surface 122.

Each layer 202 includes a first sidewall 218 extending from the corner 210. The first sidewall 218 is positioned along a top 220 of the horizontal support surface 122, such that the first sidewall 218 extends coplanar to the top 220 of the horizontal support surface 122. The first sidewall 218 extends from the corner 210 to an end 222. In the illustrative embodiment, the bottom layer 204 includes a first sidewall 224 that extends from the corner 210 coplanar to the top 220 of the horizontal support surface 122 to an end 226 that is positioned at the corner 216 of the horizontal support surface 122. The top layer 206 includes a first sidewall 228 that extends from the corner 210 coplanar to the top 220 of the horizontal support surface 122 to an end 230 that is positioned between the corner 214 of the horizontal support surface 122 and the corner 216 of the horizontal support surface 122. The first sidewall 228 of the top layer 206 extends coplanar to the first sidewall 224 of the bottom layer 204. The first sidewall 228 of the top layer 206 has a length that is less than a length of the first sidewall 224 of the bottom layer 204. When viewing the layers 202 from the top 220 of the horizontal support surface 122, each layer 202 includes a first sidewall 218 that is coplanar with the top 220 of the horizontal support surface 122 and each first sidewall 218 of the other layers 202. Moving from the bottom layer 204 to the top layer 206, the first sidewall 218 of each layer 202 is aligned at the corner 212 of the lateral rotation apparatus 200 and has a length that is less than a length of the first sidewall 218 of the layer 202 positioned below.

Each layer 202 includes a second sidewall 232 extending from the corner 210. The second sidewall 232 is substantially perpendicular to the first sidewall 218. The second sidewall 232 is positioned along a side 234 of the horizontal support surface 122, such that the second sidewall 232 extends coplanar to the side 234 of the horizontal support surface 122. The second sidewall 232 extends from the corner 210 to an end 236. In the illustrative embodiment, the bottom layer 204 includes a second sidewall 238 that extends from the corner 210 coplanar to the side 234 of the horizontal support surface 122 to an end 240 that is positioned between the corner 214 of the horizontal support surface 122 a corner 242 of the horizontal support surface 122 positioned on the side 234. The top layer 206 includes a second sidewall 244 that extends from the corner 210 coplanar to the side 234 of the horizontal support surface 122 to an end 246 that is positioned between the corner 214 of the horizontal support surface 122 and the corner 242 of the horizontal support surface 122 closer to the corner 214 than the end 240 of the second sidewall 238 of the bottom layer 204. The second sidewall 244 of the top layer 206 extends coplanar to the second sidewall 238 of the bottom layer 204. The second sidewall 244 of the top layer 206 has a length that is less than a length of the second sidewall 238 of the bottom layer 204. When viewing the layers 202 from the side 234 of the horizontal support surface 122, each layer 202 includes a second sidewall 232 that is coplanar with the side 234 of the horizontal support surface 122 and each second sidewall 232 of the other layers 202. Moving from the bottom layer 204 to the top layer 206, the second sidewall 232 of each layer 202 is aligned at the corner 212 of the lateral rotation apparatus 200 and has a length that is less than a length of the second sidewall 232 of the layer 202 positioned below.

Figure 6:
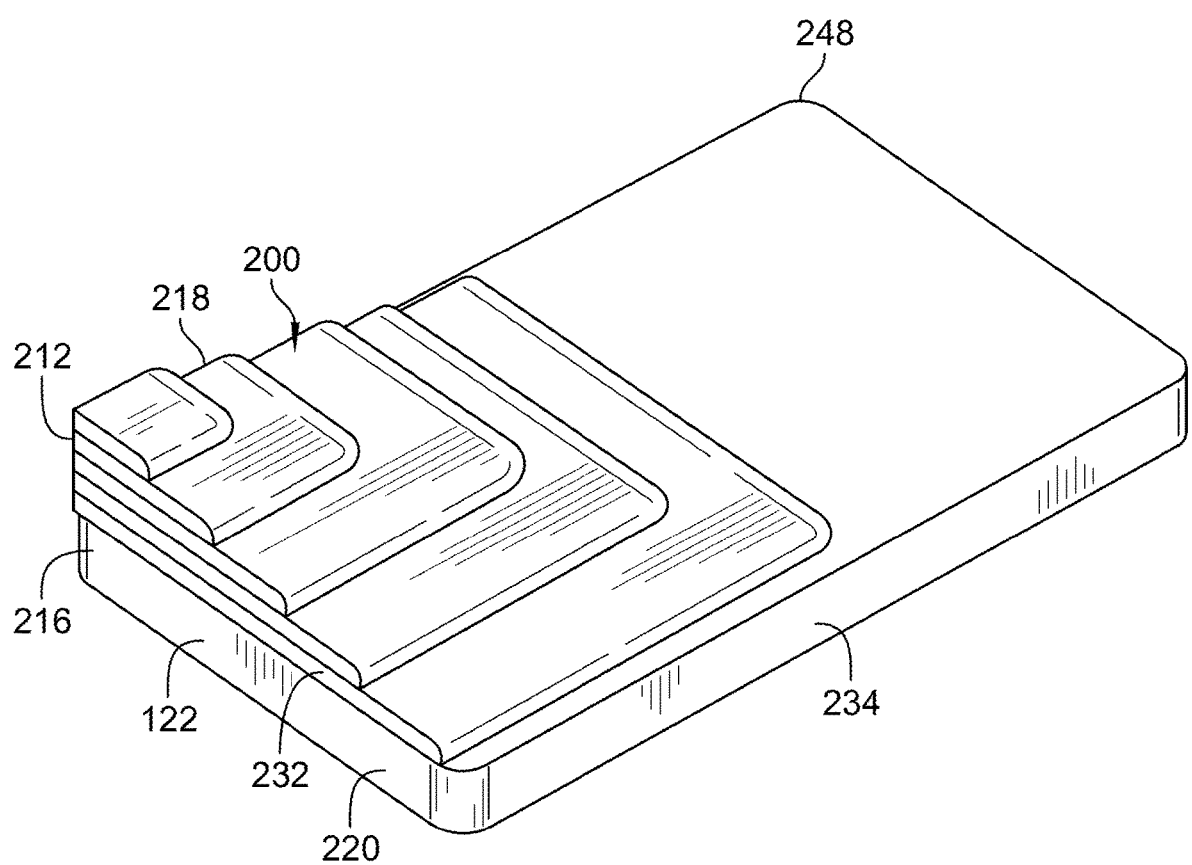
FIG. 6 is perspective view from the top of the horizontal support surface of the lateral rotation apparatus shown in FIG. 2 and rotated to an opposite side of the horizontal support surface.

It should be noted that the lateral rotation apparatus 200 may be rotated so that the corner 212 of the lateral rotation apparatus 200 may align with an opposite corner 216 of the horizontal support surface 122, as illustrated in FIG. 6. In such an embodiment, the first sidewall 218 of each layer may be positioned coplanar with a side 248 of the horizontal support surface 122 that is opposite the side 234. Also, the second sidewall 232 of each layer 202 may be positioned coplanar with the top 220 of the horizontal support surface 122.

Each layer 202 includes an angled sidewall 250 that extends from the end 222 of the first sidewall 218 to the end 236 of the second sidewall 238. The angled sidewall 250 is angled from a bottom 252 of the layer 202 to a top 254 of the layer 202. The angled sidewall 250 may be formed in the shape of a curve between the end 222 and the end 236. The angled sidewall 250 of the bottom layer 204 is not coplanar with the angled sidewall 250 of any other layer 202. Moving from the bottom layer 204 to the top layer 206, the angled sidewall 250 of each layer 202 is positioned closer to the corner 212 of the lateral rotation apparatus 200 than the previous lower layer 202. For example, the angled sidewall 250 of the bottom layer 204 is positioned a further distance from the corner 212 than the angled sidewall 250 of the top layer 206. The angled sidewalls 250 of each layer 202 form an angled sidewall 260 of the lateral rotation apparatus 200 that gradually increases in height from the bottom layer 204 to the top layer 206 such that the lateral rotation apparatus 200 has a maximum height at the top layer 206 and a minimum height at the ends 226, 240 of the bottom layer 204. Because the bottom layer 204 has a greater area than the top layer 206, the thickness of the lateral rotation apparatus 200 is greater at the corner 212 than a thickness of the lateral rotation apparatus 200 at the end 226 of the first sidewall 224 of the bottom layer 204. The thickness of the lateral rotation apparatus 200 gradually decreases from the corner 212 to the end 226 of the first sidewall 224 of the bottom layer 204. Additionally, a thickness of the lateral rotation apparatus 200 is greater at the corner 212 than a thickness of the lateral rotation apparatus 200 at the end 240 of the second sidewall 238 of the bottom layer 204. The thickness of the lateral rotation apparatus 200 gradually decreases from the corner 212 to the end 240 of the second sidewall 238 of the bottom layer 204. Moreover, the thickness of the lateral rotation apparatus 200 gradually decreases from the top 254 of the angled sidewall 250 of the top layer 206 to the bottom 252 of the angled sidewall 250 of the bottom layer 204.

Figure 7:
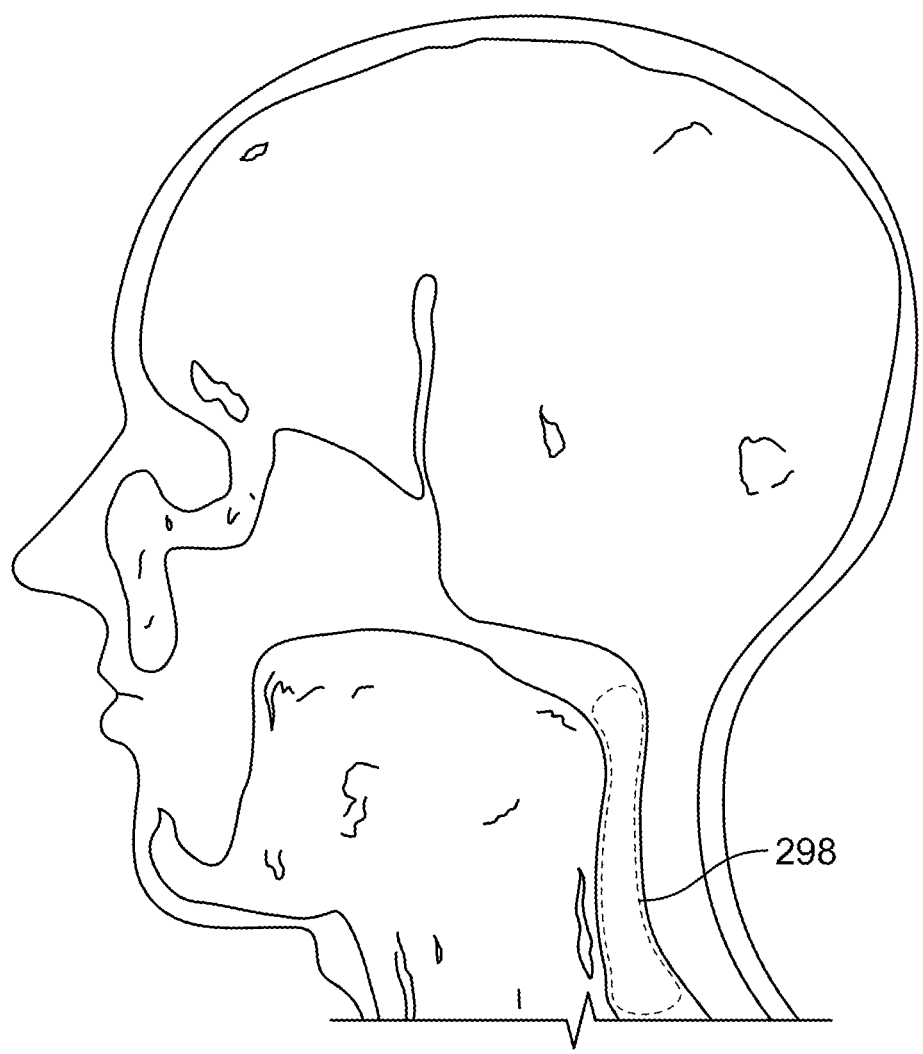
FIG. 7 is an MRI of a user laying on a support system in accordance with an embodiment.

Referring to FIG. 7, a sagittal distance 298 is defined in the airway of a user. The sagittal distance 298 is defined as an area of the user's esophagus that is opened while the user is laying on the support system 100. As illustrated in the graphs described below, the head tilt angle, the torso tilt angle and the leg tilt angle affects the sagittal distance 298 of the user.

Figure 8:
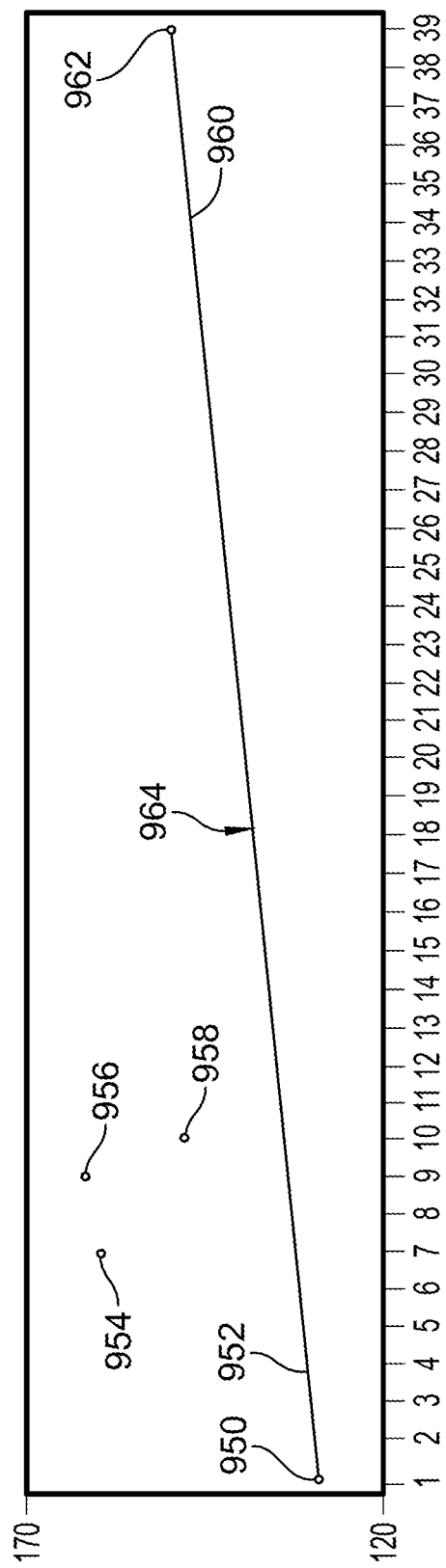
FIG. 8 is a graph is provided showing a minimum airway area in relation to various tilt angles.

Referring to FIG. 8, a graph is provided showing a minimum airway area in relation to various tilt angles. Based on prior research in the field of sleep medicine, it was believed that a subject with Positional Obstructive Sleep Apnea (POSA) will suffer a disproportionate number of Apnea-Hypopnea Index events (or number of airway obstructions) when in the supine position than in the non-supine positon (i.e., upper airway rotated 90 degrees away from vertical). It has been assumed that changes in the airway would be either linear as the upper airway is rotated from vertical to 90 degrees from vertical, or more likely that the relationship be more binary, and that changes in the upper airway would be primarily seen once the upper airway was rotated to at or about 90 degrees from vertical.

However, based on research using Magnetic Resonance Imaging of the upper airways of patient previously diagnosed with POSA, this was not the case. Rather, in relevant measurements of the upper airway (for example, measurement of the minimum airway area in the retroglossal region), the relationship between head/torso support and minimum airway area was neither linear nor binary between 0 degree and 90 degree positons. As illustrated in FIG. 8, the research found that minimum airway area increased much more rapidly than a linear relationship and reached that level of improvement far before the 90 degree positon.

From point 950 (head angle at 0 degrees, torso angle at 0 degrees), head angle increases by 2.5 degrees until it is 5 degrees greater than the torso angle, so at point 952 the head angle is at 5 degrees and the torso angle is at 0 degrees, after which the head and torso angles each increase by 2.5 degrees until the head degree reaches 90 degrees at point 960, after which the torso angle increases by 2.5 degrees until both the head and torso angles are at 90 degrees at point 962. In FIG. 8, minimum airway area is plotted at point 950 (head angle at 0 degrees, torso angle at 0 degrees), point 954 (head angle at 15 degrees, torso angle at 10 degrees), point 956 (head angle at 20 degrees, torso angle at 15 degrees), point 958 (head angle at 22.5 degrees, torso angle at 17.5 degrees) and point 962 (head angle at 90 degrees, torso angle at 90 degrees), with the linear extrapolation between the measurements at point 950 and point 962 shown as line 964.

Referring to FIGS. 9-12, specific examples of measured sagittal distances 998 are represented through a series of graphs. It should be noted that the examples and data represented in the graphs of FIGS. 9-12 are exemplary only and non-limiting. It will be appreciated that various studies may be provided that result in other examples of data.

Figure 9:
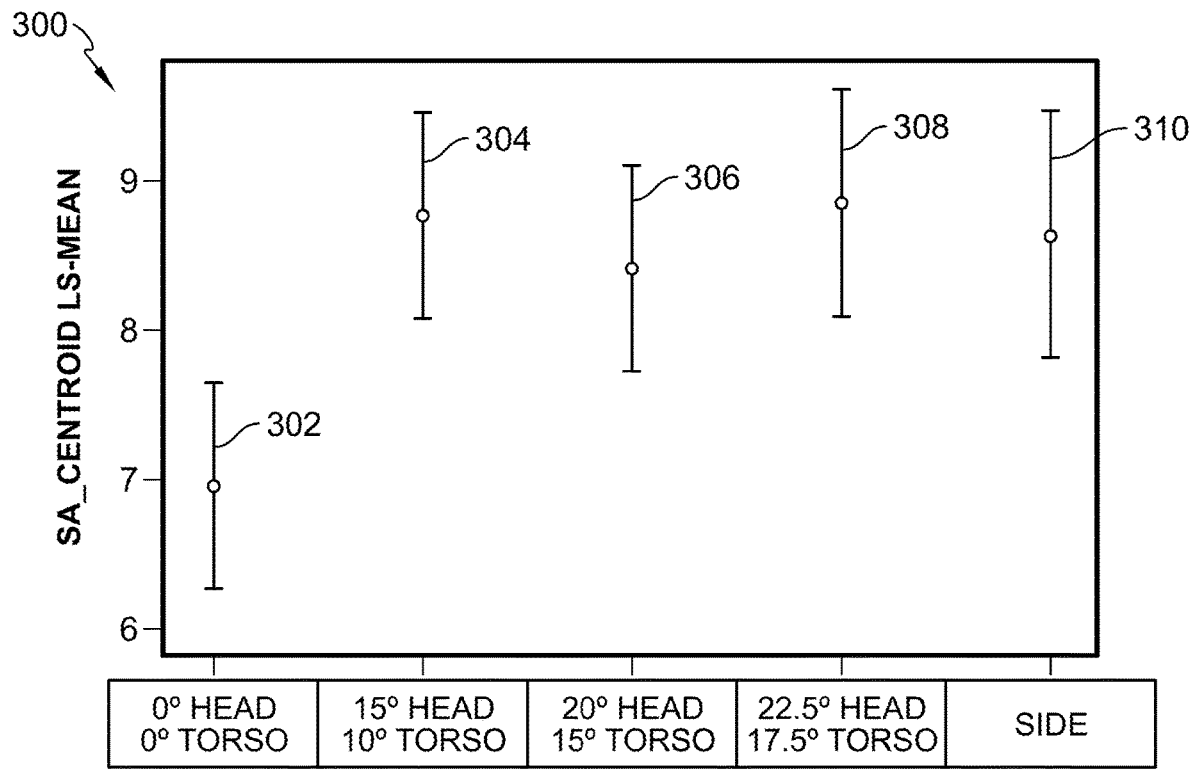
FIG. 9 is a graph of sleep surface orientations versus a minimum sagittal distance taken in a retroglossal region of a user positioned on the sleep surface.

Referring to FIG. 9, the graph 300 illustrates sleep orientations on the x-axis versus a minimum sagittal distance on the y-axis in the retroglossal region of a user positioned on the sleep surface 114. As illustrated by line 302, the minimum sagittal distance for a user in the supine position with the head at 0° with respect to the horizontal support plane 124 and the torso at 0° with respect to the horizontal support plane 124 is between approximately 6.25 mm$^2$ and approximately 7.75 mm$^2$ with a mean minimum sagittal distance of approximately 7 mm$^2$. As illustrated by line 304, the minimum sagittal distance for a user with the lateral rotation apparatus rotating the head at 15° with respect to the horizontal support plane 124 and rotating the torso at 10° with respect to the horizontal support plane 124 is between approximately 8 mm$^2$ and approximately 9.5 mm$^2$ with a mean minimum sagittal distance of approximately 8.75 mm$^2$. As illustrated by line 306, the minimum sagittal distance for a user with the lateral rotation apparatus rotating the head at 20° with respect to the horizontal support plane 124 and rotating the torso at 15° with respect to the horizontal support plane 124 is between approximately 7.75 mm$^2$ and approximately 9 mm$^2$ with a mean minimum sagittal distance of approximately 8.5 mm$^2$. As illustrated by line 308, the minimum sagittal distance for a user with the lateral rotation apparatus rotating the head at 22.5° with respect to the horizontal support plane 124 and rotating the torso at 17.5° with respect to the horizontal support plane 124 is between approximately 8 mm$^2$ and approximately 9.75 mm$^2$ with a mean minimum sagittal distance of approximately 8.75 mm$^2$. As illustrated by line 310, the minimum sagittal distance for a user lying on their side is between approximately 7.75 mm$^2$ and approximately 9.5 mm$^2$ with a mean minimum sagittal distance of approximately 8.5 mm$^2$. Accordingly, the user of the sleep surface 114 has a greater minimum sagittal distance when lying with the head at 22.5° with respect to the horizontal support plane 124 and rotating the torso at 17.5° with respect to the horizontal support plane 124 or when lying with the head at 15° with respect to the horizontal support plane 124 and rotating the torso at 10° with respect to the horizontal support plane 124. In all positions on the lateral rotation apparatus 200, the user has a greater minimum sagittal distance when compared to lying supine.

Figure 10:
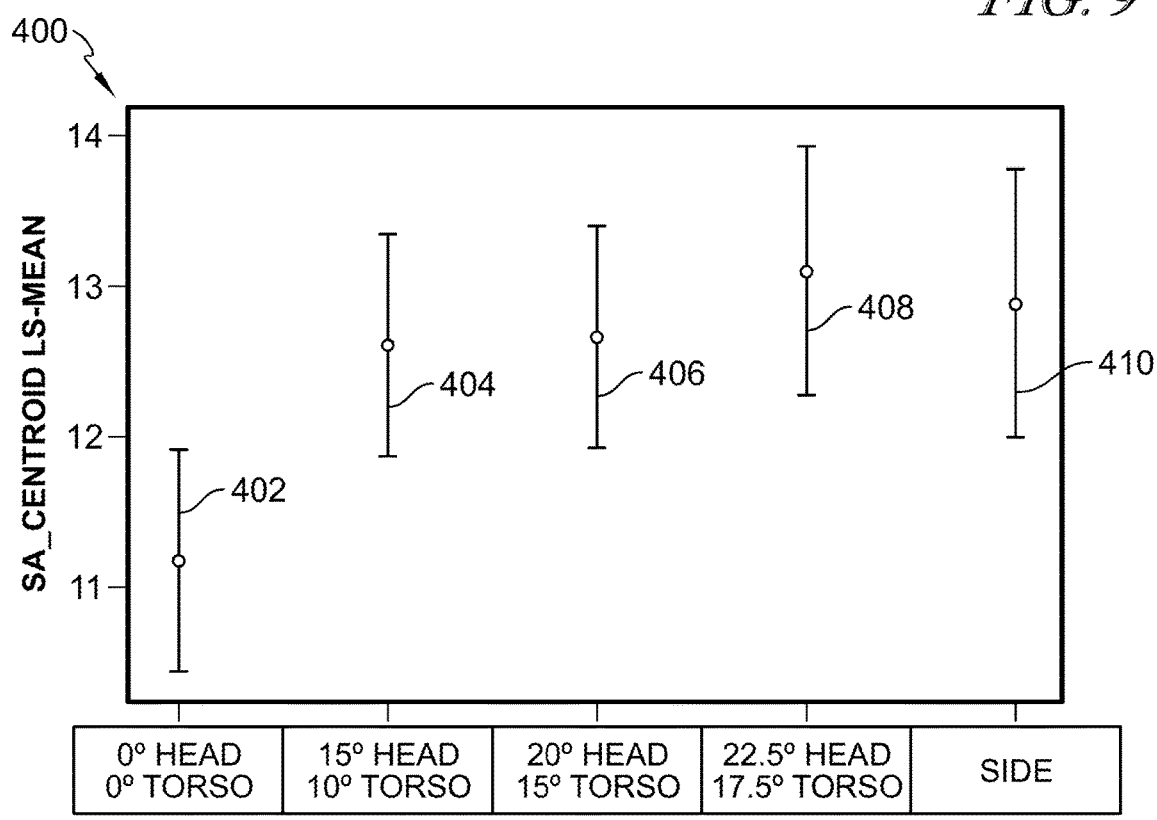
FIG. 10 is a graph of sleep surface orientations versus an average sagittal distance taken in a retroglossal region of a user positioned on the sleep surface.

Referring to FIG. 10, the graph 400 illustrates sleep orientations on the x-axis versus an average sagittal distance on the y-axis taken in a retroglossal region of a user positioned on the sleep surface 114. As illustrated by line 402, the average sagittal distance for a user in the supine position with the head at 0° with respect to the horizontal support plane 124 and the torso at 0° with respect to the horizontal support plane 124 is between approximately 10.25 mm$^2$ and approximately 11.75 mm$^2$ with a mean average sagittal distance of approximately 11.25 mm$^2$. As illustrated by line 404, the average sagittal distance for a user with the lateral rotation apparatus rotating the head at 15° with respect to the horizontal support plane 124 and rotating the torso at 10° with respect to the horizontal support plane 124 is between approximately 11.75 mm$^2$ and approximately 13.5 mm$^2$ with a mean average sagittal distance of approximately 12.5 mm$^2$. As illustrated by line 406, the average sagittal distance for a user with the lateral rotation apparatus rotating the head at 20° with respect to the horizontal support plane 124 and rotating the torso at 15° with respect to the horizontal support plane 124 is between approximately 11.75 mm$^2$ and approximately 13.5 mm$^2$ with a mean average sagittal distance of approximately 12.5 mm$^2$. As illustrated by line 408, the average sagittal distance for a user with the lateral rotation apparatus rotating the head at 22.5° with respect to the horizontal support plane 124 and rotating the torso at 17.5° with respect to the horizontal support plane 124 is between approximately 12.25 mm$^2$ and approximately 13.75 mm$^2$ with a mean average sagittal distance of approximately 13.25 mm$^2$. As illustrated by line 410, the average sagittal distance for a user lying on their side is between approximately 12 mm$^2$ and approximately 13.75 mm$^2$ with a mean average sagittal distance of approximately 12.75 mm$^2$. Accordingly, the user of the sleep surface 114 has a greater average sagittal distance when lying with the head at 22.5° with respect to the horizontal support plane 124 and rotating the torso at 17.5° with respect to the horizontal support plane 124. In all positions on the lateral rotation apparatus 200, the user has a greater average sagittal distance when compared to lying supine.

Figure 11:
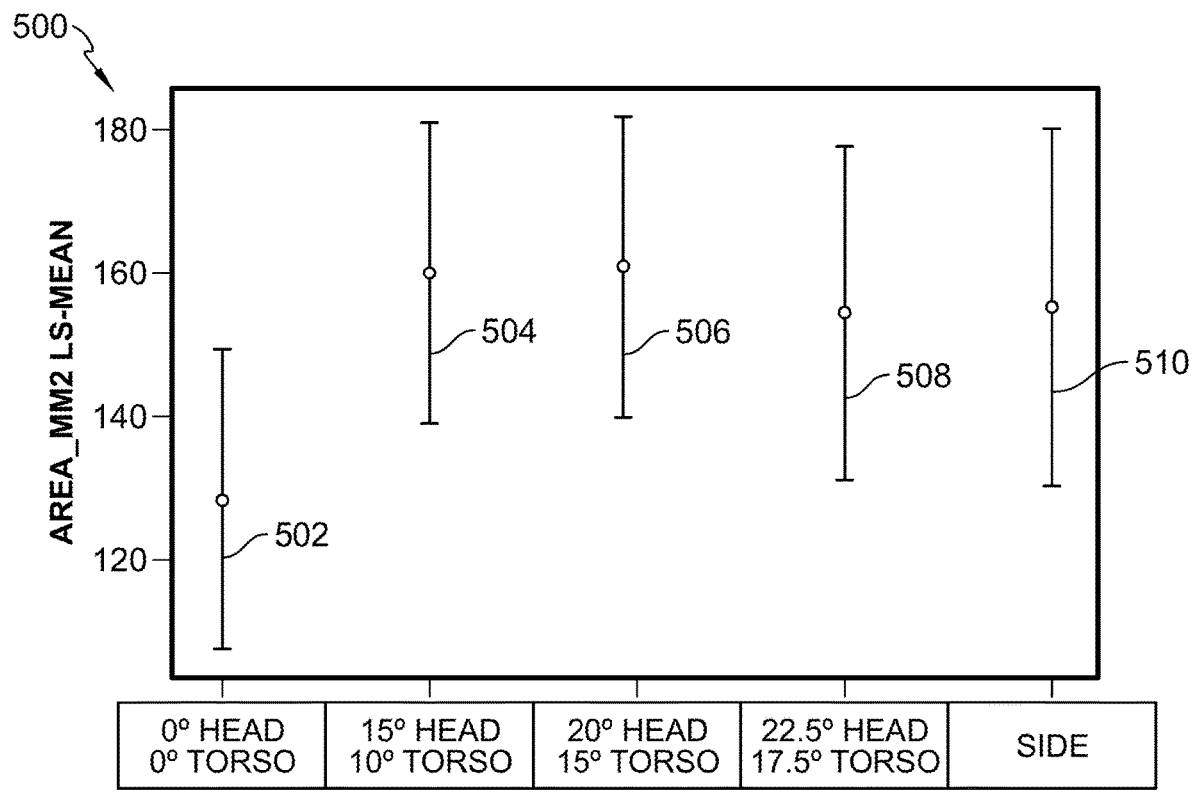
FIG. 11 is a graph of sleep surface orientations versus a minimum airway area taken in a retroglossal region of a user positioned on the sleep surface.

Referring to FIG. 11, the graph 500 illustrates sleep orientations on the x-axis versus a minimum airway area on the y-axis taken in the retroglossal region of a user positioned on the sleep surface 114. As illustrated by line 502, the minimum airway area in the retroglossal region for a user in the supine position with the head at 0° with respect to the horizontal support plane 124 and the torso at 0° with respect to the horizontal support plane 124 is between approximately 105 mm$^2$ and approximately 150 mm$^2$ with a mean minimum airway area in the retroglossal region of approximately 130 mm$^2$. As illustrated by line 504, the minimum airway area in the retroglossal region for a user with the lateral rotation apparatus rotating the head at 15° with respect to the horizontal support plane 124 and rotating the torso at 10° with respect to the horizontal support plane 124 is between approximately 140 mm$^2$ and approximately 180 mm$^2$ with a mean minimum airway area in the retroglossal region of approximately 160 mm$^2$. As illustrated by line 506, the minimum airway area in the retroglossal region for a user with the lateral rotation apparatus rotating the head at 20° with respect to the horizontal support plane 124 and rotating the torso at 15° with respect to the horizontal support plane 124 is between approximately 140 mm² and approximately 185 mm² with a mean minimum airway area in the retroglossal region of approximately 185 mm². As illustrated by line 508, the minimum airway area in the retroglossal region for a user with the lateral rotation apparatus rotating the head at 22.5° with respect to the horizontal support plane 124 and rotating the torso at 17.5° with respect to the horizontal support plane 124 is between approximately 130 mm² and approximately 175 mm² with a mean minimum airway area in the retroglossal region of approximately 155 mm². As illustrated by line 510, the minimum airway area in the retroglossal region for a user lying on their side is between approximately 130 mm² and approximately 180 mm² with a mean minimum airway area in the retroglossal region of approximately 155. In all positions on the lateral rotation apparatus 200, the user has a greater average sagittal distance when compared to lying supine. For example, the user of the sleep surface 114 has a 24.6% greater mean minimum airway area than lying supine when lying with the head at 15° with respect to the horizontal support plane 124 and the torso at 10° with respect to the horizontal support plane 124 or when lying with the head at 20° with respect to the horizontal support plane 124 and the torso at 15° with respect to the horizontal support plane 124.

Figure 12:
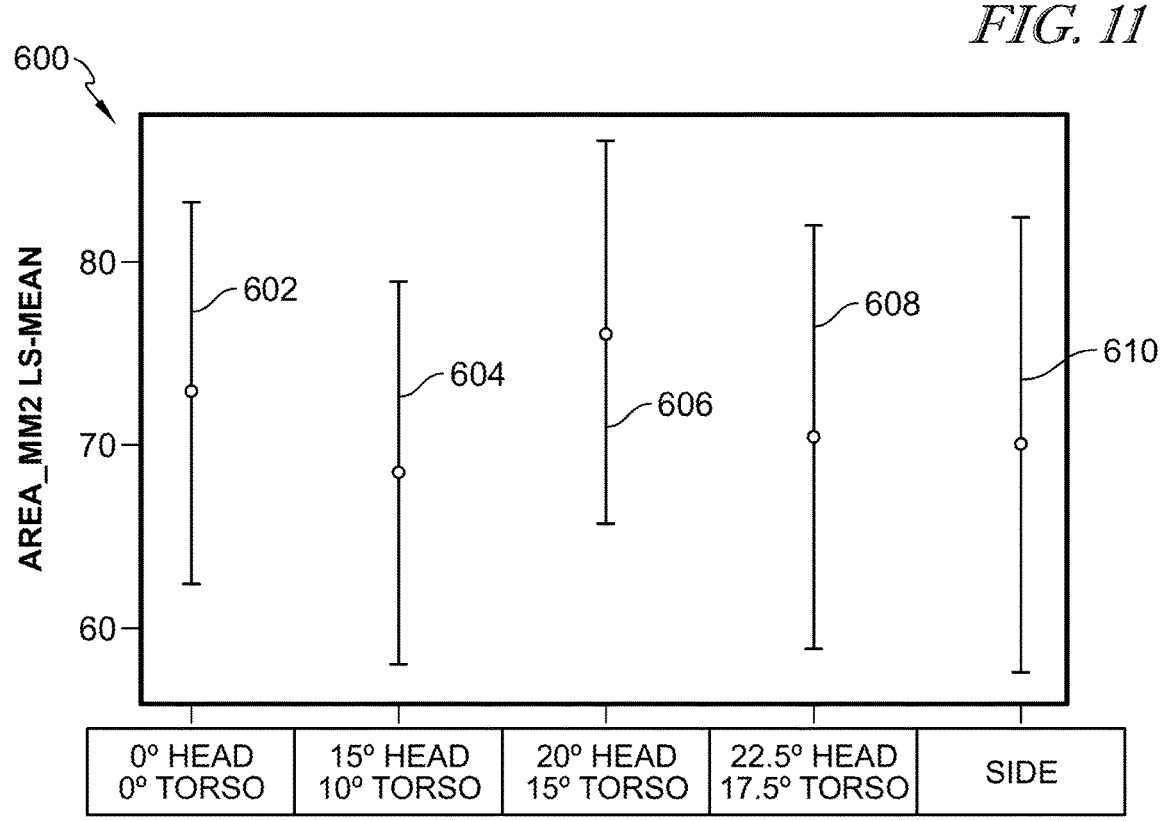
FIG. 12 is a graph of sleep surface orientations versus a minimum airway area taken in a retropalatal region of a user positioned on the sleep surface.

Referring to FIG. 12, the graph 600 illustrates sleep orientations on the x-axis versus a minimum airway area on the y-axis taken in the retropalatal region of a user positioned on the sleep surface 114. As illustrated by line 602, the minimum airway area in the retropalatal region for a user in the supine position with the head at 0° with respect to the horizontal support plane 124 and the torso at 0° with respect to the horizontal support plane 124 is between approximately 62.5 mm² and approximately 85 mm² with a mean minimum airway area in the retropalatal region of approximately 72.5 mm². As illustrated by line 504, the minimum airway area in the retropalatal region for a user with the lateral rotation apparatus rotating the head at 15° with respect to the horizontal support plane 124 and rotating the torso at 10° with respect to the horizontal support plane 124 is between approximately 57.5 mm² and approximately 77.5 mm² with a mean minimum airway area in the retropalatal region of approximately 67.5 mm². As illustrated by line 506, the minimum airway area in the retropalatal region for a user with the lateral rotation apparatus rotating the head at 20° with respect to the horizontal support plane 124 and rotating the torso at 15° with respect to the horizontal support plane 124 is between approximately 65 mm² and approximately 87.5 mm² with a mean minimum airway area in the retropalatal region of approximately 75 mm². As illustrated by line 508, the minimum airway area in the retropalatal region for a user with the lateral rotation apparatus rotating the head at 22.5° with respect to the horizontal support plane 124 and rotating the torso at 17.5° with respect to the horizontal support plane 124 is between approximately 57.5 mm² and approximately 82.5 mm² with a mean minimum airway area in the retropalatal region of approximately 70 mm². As illustrated by line 510, the minimum airway area for a user lying on their side is between approximately 55 mm² and approximately 82.5 mm² with a mean minimum airway area in the retropalatal region of approximately 70 mm². The user of the sleep surface 114 has a greater mean minimum airway area in the retropalatal region than lying supine when lying with the head at 20° with respect to the horizontal support plane 124 and the torso at 15° with respect to the horizontal support plane 124.

Figure 13A:
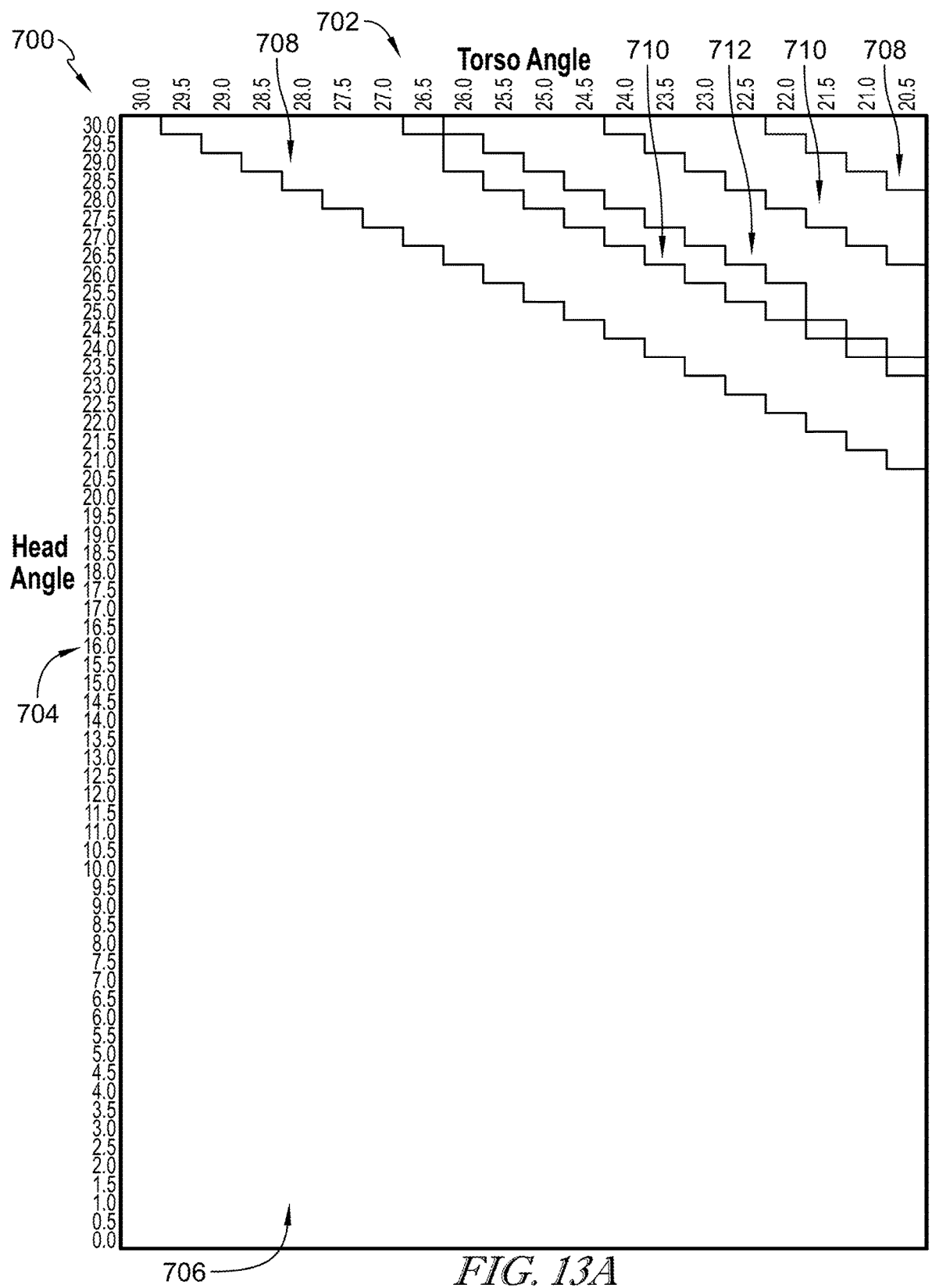
FIGS. 13A-13C illustrate an exemplary matrix of torso angles versus head angles that may be used to improve POSA and reduce the number of Apnea-Hypopnea Index events.
Figure 13B:
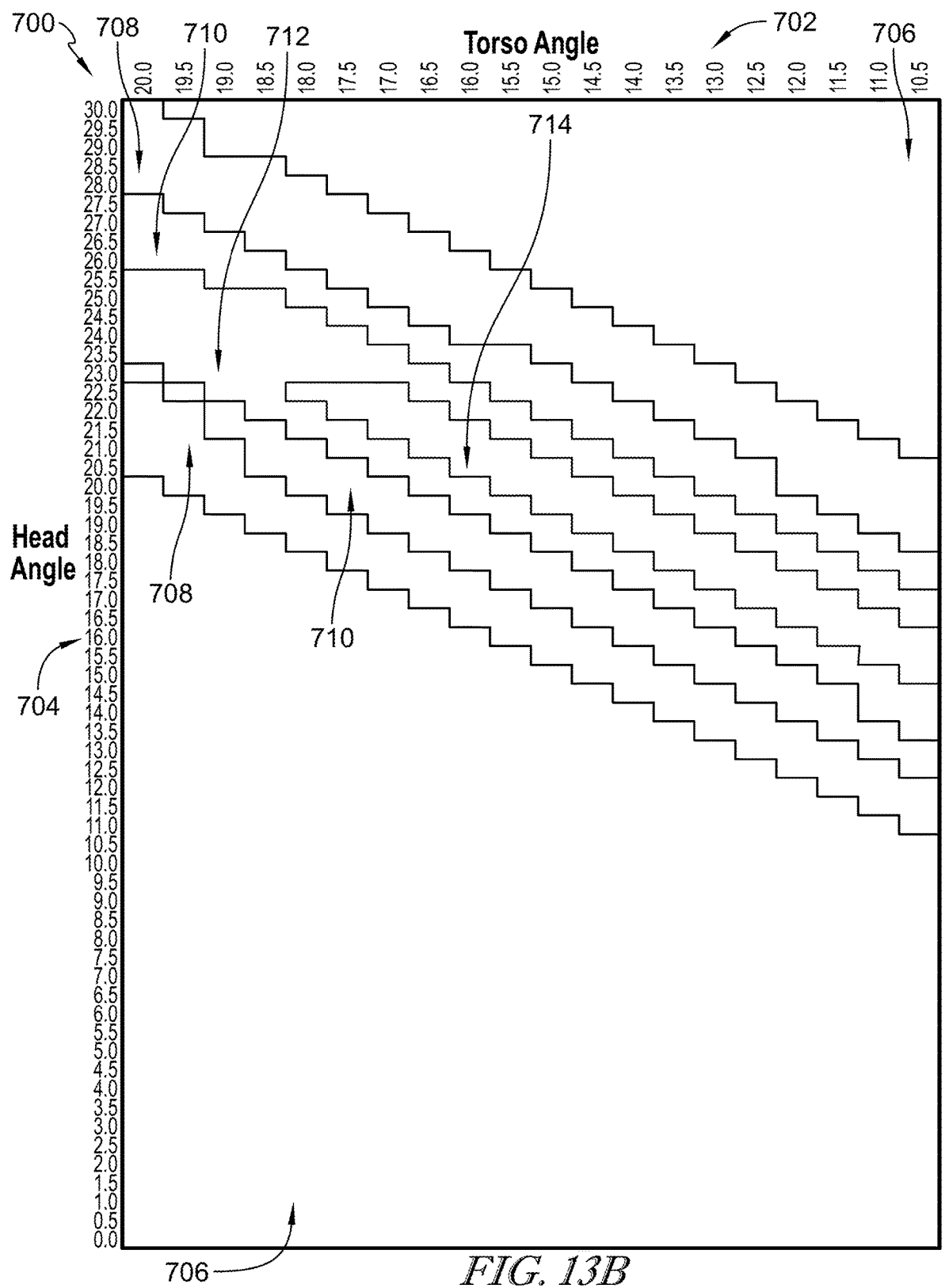
Figure 13C:
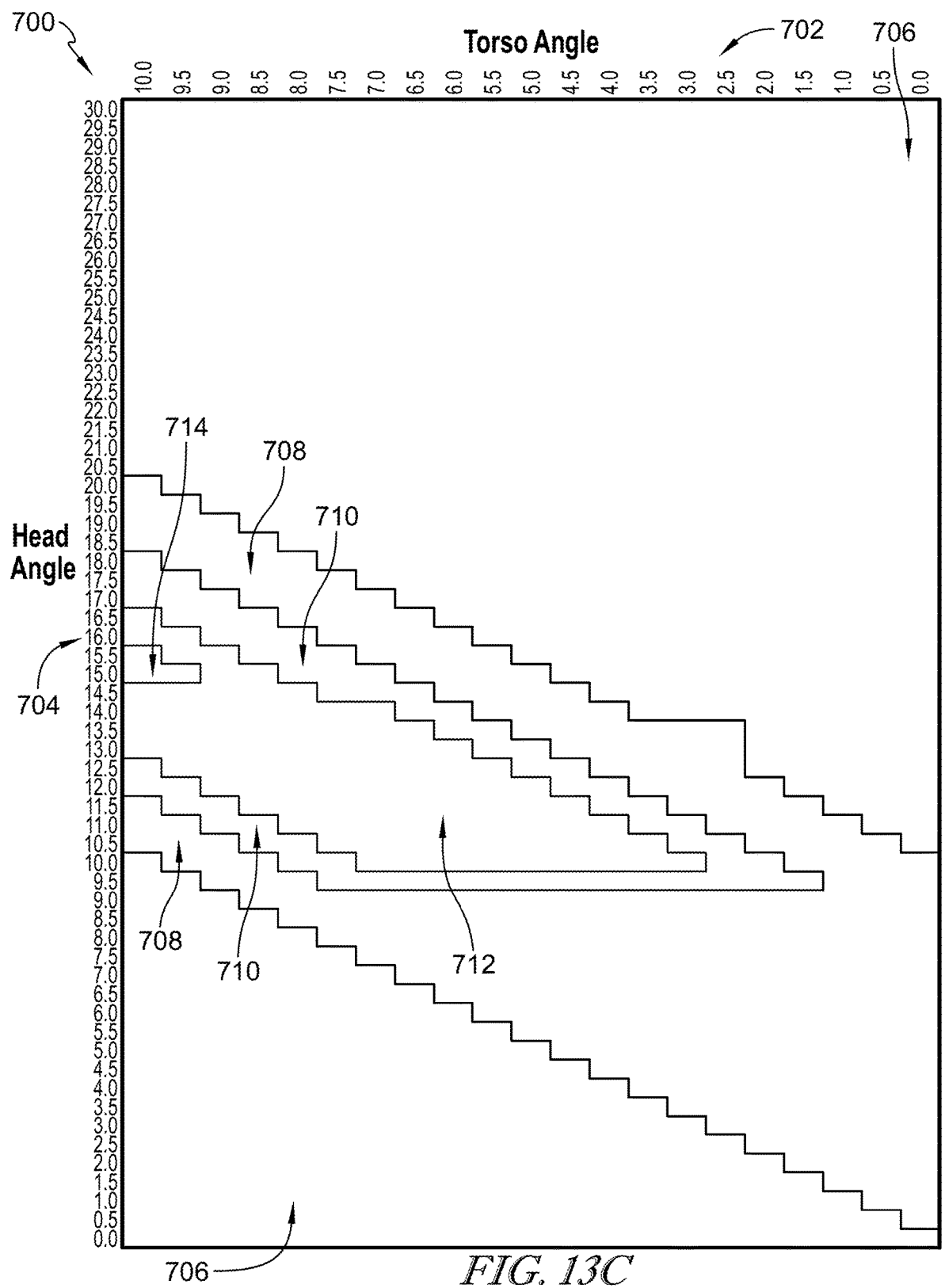

FIGS. 13A-13C illustrate an exemplary matrix 700 of torso angles 702 versus head angles 704 that may be used to improve POSA and reduce the number of Apnea-Hypopnea Index events. The area 706 illustrates combinations of torso angles 702 and head angles 704 that are generally considered unacceptable for improving POSA and reducing the number of Apnea-Hypopnea Index events. The area 708 illustrates combinations of torso angles 702 and head angles 704 that are generally considered suboptimal for improving POSA and reducing the number of Apnea-Hypopnea Index events. The area 710 illustrates combinations of torso angles 702 and head angles 704 that are generally considered good or fair for improving POSA and reducing the number of Apnea-Hypopnea Index events. The area 712 illustrates combinations of torso angles 702 and head angles 704 that are generally considered very good for improving POSA and reducing the number of Apnea-Hypopnea Index events. The area 714 illustrates combinations of torso angles 702 and head angles 704 that are generally considered excellent for improving POSA and reducing the number of Apnea-Hypopnea Index events.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The invention claimed is:
1. A lateral rotation apparatus, comprising:
   a person support surface comprising head, torso and leg segments each having an independently rotatable person support plane;
   a wedge positioned below the person support surface, the wedge comprising a bottom layer having a first sidewall, a second sidewall, and a first angled sidewall extending between the first sidewall and the second sidewall, the wedge further comprising a top layer having a third sidewall, a fourth sidewall, and a second angled sidewall extending between the third sidewall and the fourth sidewall, the wedge further comprising a corner where the first sidewall and the second sidewall of the bottom layer meet and the third sidewall and the fourth sidewall of the top layer meet, wherein the first angled sidewall of the bottom layer is positioned a further distance from the corner than the second angled sidewall of the top layer, the wedge operable to:
   rotate the head segment of the person support surface to a head tilt angle approximately at a centerline of the head segment in the range of about 7° to about 30° relative to a horizontal support plane; and rotate the torso segment of the person support surface to a torso tilt angle approximately at a centerline of the torso segment that is within a range of about 5° to about 10° less than the head tilt angle, wherein the wedge provides a graduated lateral rotation of the person support surface.

2. The lateral rotation apparatus of claim 1, wherein the first sidewall is substantially perpendicular to the second sidewall, wherein a thickness of the wedge is greater at the corner than a thickness of the wedge at an end of the first sidewall.

3. The lateral rotation apparatus of claim 2, wherein the thickness of the wedge gradually decreases from the corner to the end of the first sidewall.

4. The lateral rotation apparatus of claim 2, wherein a thickness of the wedge is greater at the corner than a thickness of the wedge at an end of the second sidewall.

5. The lateral rotation apparatus of claim 4, wherein the thickness of the wedge gradually decreases from the corner to the end of the second sidewall.

6. The lateral rotation apparatus of claim 1, wherein the wedge comprises a plurality of layers stacked on one another.

7. The lateral rotation apparatus of claim 6, wherein each of the plurality of layers has a different area.

8. The lateral rotation apparatus of claim 1, wherein the bottom layer has a greater area than an area of the top layer positioned on the bottom layer.

9. The lateral rotation apparatus of claim 1, wherein the third sidewall of the top layer is coplanar with the first sidewall of the bottom layer, the first sidewall of the bottom layer being longer than the third sidewall of the top layer.

10. The lateral rotation apparatus of claim 1, wherein the fourth sidewall of the top layer is coplanar with the second sidewall of the bottom layer, the second sidewall of the bottom layer being longer than the fourth sidewall of the top layer.

11. The lateral rotation apparatus of claim 1, wherein the first sidewall of the bottom layer is substantially perpendicular to the second sidewall of the bottom layer, and the third sidewall of the top layer is substantially perpendicular to the fourth sidewall of the top layer.

12. The lateral rotation apparatus of claim 1, wherein the first angled sidewall connects ends of the first sidewall and the second sidewall of the bottom layer, and the second angled sidewall connects ends of the third sidewall and the fourth sidewall of the top layer.

13. The lateral rotation apparatus of claim 1, wherein the first angled sidewall of the bottom layer is not coplanar with the second angled sidewall of the top layer.

14. The lateral rotation apparatus of claim 1, wherein the torso segment is rotated to a torso tilt angle approximately at a centerline of the torso segment in the range of about 0° to about 25°.

15. The lateral rotation apparatus of claim 1, wherein the head segment is rotated to a head tilt angle approximately at a centerline of the head segment in the range of about 10° to about 15°.

16. The lateral rotation apparatus of claim 15, wherein the torso segment is rotated to a torso tilt angle approximately at a centerline of the torso segment in the range of about 5° to about 10°.

17. The lateral rotation apparatus of claim 1, wherein the leg segment is rotated to a leg tilt angle approximately at a centerline of the leg segment in the range of about 0° to about 5°.

18. The lateral rotation apparatus of claim 1, wherein the person support surface comprises a support material having a density, and the head tilt angle is a function of the density of the support material.

19. The lateral rotation apparatus of claim 18, wherein the torso tilt angle is a function of the density of the support material.

20. A lateral rotation apparatus, comprising:
a person support surface comprising head, torso and leg segments each having an independently rotatable person support plane;
a wedge positioned below the person support surface, wherein the wedge comprises a plurality of layers stacked on one another, wherein a bottom layer has a greater area than an area of a top layer positioned on the bottom layer, wherein the bottom layer comprises a first sidewall and the top layer comprises a first sidewall that is coplanar with the first sidewall of the bottom layer, the first sidewall of the bottom layer being longer than the first sidewall of the top layer, wherein the bottom layer comprises a second sidewall and the top layer comprises a second sidewall that is coplanar with the second sidewall of the bottom layer, the second sidewall of the bottom layer being longer than the second sidewall of the top layer, wherein the bottom layer further comprises an angled sidewall connecting ends of the first sidewall and the second sidewall of the bottom layer, and the top layer further comprises an angled sidewall connecting ends of the first sidewall and the second sidewall of the top layer, wherein the wedge further comprises a corner where the first sidewall and the second sidewall of the bottom layer meet and the first sidewall and the second sidewall of the top layer meet, wherein the angled sidewall of the bottom layer is positioned a further distance from the corner than the angled sidewall of the top layer, the wedge operable to:
rotate the head segment of the person support surface to a head tilt angle approximately at a centerline of the head segment in the range of about 7° to about 30° relative to a horizontal support plane; and
rotate the torso segment of the person support surface to a torso tilt angle approximately at a centerline of the torso segment that is within a range of about 5° to about 10° less than the head tilt angle,
wherein the wedge provides a graduated lateral rotation of the person support surface.

\* \* \* \* \*

UNITED STATES PATENT AND TRADEMARK OFFICE
CERTIFICATE OF CORRECTION

PATENT NO.       : 11,007,098 B2
APPLICATION NO.  : 16/022846
DATED            : May 18, 2021
INVENTOR(S)      : David L. Ribble and Kirsten M. Emmons Page 1 of 1

It is certified that error appears in the above-identified patent and that said Letters Patent is hereby corrected as shown below:

On the Title Page

On Page 2, under (56), References Cited, OTHER PUBLICATIONS, Second Column, Line 22, delete "Hournal" and insert in its place --Journal--.

On Page 3, under (56), References Cited, OTHER PUBLICATIONS, Second Column, Line 62, delete "Otorhinolaryngol" and insert in its place --Otorhinolaryngology--.

On Page 4, under (56), References Cited, OTHER PUBLICATIONS, First Column, Line 47, delete "Otorhinolaryngol" and insert in its place --Otorhinolaryngology--.

On Page 5, under (56), References Cited, OTHER PUBLICATIONS, Second Column, Line 12, delete "Otolaryngol" and insert in its place --Otolaryngology--.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*